(12) United States Patent
Guo et al.

(10) Patent No.: US 11,939,571 B2
(45) Date of Patent: Mar. 26, 2024

(54) LIBRARY-SCALE ENGINEERING OF METABOLIC PATHWAYS

(71) Applicant: President and Fellows of Harvard College, Cambridge, MA (US)

(72) Inventors: Xiaoge Guo, Brookline, MA (US); Alejandro Chavez, New York, NY (US); Max Schubert, Brookline, MA (US); Eric Kelsic, Boston, MA (US)

(73) Assignees: President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 1507 days.

(21) Appl. No.: 16/307,998

(22) PCT Filed: Jun. 12, 2017

(86) PCT No.: PCT/US2017/036985
§ 371 (c)(1),
(2) Date: Dec. 7, 2018

(87) PCT Pub. No.: WO2017/214615
PCT Pub. Date: Dec. 14, 2017

(65) Prior Publication Data
US 2019/0264196 A1 Aug. 29, 2019

Related U.S. Application Data

(60) Provisional application No. 62/348,438, filed on Jun. 10, 2016.

(51) Int. Cl.
*C12N 15/10* (2006.01)
*C12N 15/00* (2006.01)
*C12N 15/86* (2006.01)
*C12N 15/90* (2006.01)
*C40B 40/08* (2006.01)

(52) U.S. Cl.
CPC .......... *C12N 15/1037* (2013.01); *C12N 15/00* (2013.01); *C12N 15/102* (2013.01); *C12N 15/1058* (2013.01); *C12N 15/86* (2013.01); *C12N 15/905* (2013.01); *C12N 2310/20* (2017.05); *C12N 2800/80* (2013.01); *C40B 40/08* (2013.01)

(58) Field of Classification Search
None
See application file for complete search history.

(56) References Cited

U.S. PATENT DOCUMENTS

| 10,266,849 B2 * | 4/2019 | Gill ....................... C12N 15/111 |
| 2004/0126883 A1 | 7/2004 | Liu |
| 2006/0051789 A1 | 3/2006 | Kazakov et al. |
| 2008/0287320 A1 | 11/2008 | Baynes et al. |
| 2014/0004567 A1 | 1/2014 | Hartley et al. |

FOREIGN PATENT DOCUMENTS

WO 2015/123339 A1 8/2015

OTHER PUBLICATIONS

Dicarlo et al., "Genome engineering in Saccharomyces cerevisiae using CRISPR-Cas systems" 41(7) Nucleic Acids Research 4336-4343 (Year: 2013).*

* cited by examiner

*Primary Examiner* — Nancy J Leith
(74) *Attorney, Agent, or Firm* — Banner & Witcoff, Ltd.

(57) ABSTRACT

Expressing guide nucleic acids (e.g., gRNA) from the same oligonucleotide that contains donor sequence permits the high efficiency, simultaneous transformation of a population of cells with both substrates. Using oligonucleotide chip array technology, one can construct thousands of oligonucleotides with customized gRNA and donor sequence in a cost effective manner. In combination, one can efficiently modify endogenous and exogenous genes.

6 Claims, 12 Drawing Sheets
Specification includes a Sequence Listing.

Sample oligos with customizable guides and donors

| | BsmBI | guide | SapI | 80 nt donor | BsmBI |
|---|---|---|---|---|---|
| Oligo 1 | cgtctc ggatc (SEQ ID NO: 42) | GCCGTCACAT AACTTAAGAA (SEQ ID NO: 43) | gtttgaagagc atacgctcttc tcca (SEQ ID NO: 44) | GGATAGCCTGGAATACGAAATCTTTGTCTT CCTGTAAAGTTACCGCCTTGTGTGTACGTG TATGATTTTTAAATATATA (SEQ ID NO: 45) | ACATCg agacg (SEQ ID NO: 48) |
| Oligo 2 | cgtctc ggatc (SEQ ID NO: 42) | AAGGGAGCAC AAATGGTTAA (SEQ ID NO: 46) | gtttgaagagc atacgctcttc tcca (SEQ ID NO: 44) | TCGCGATGTGCTTTTGGATAGCCTGGAATA CGAAATCTTTCGGCTTCGTCACCATTACCG CCTTGTGTGTACGTGTATGA (SEQ ID NO: 47) | ACATCg agacg (SEQ ID NO: 48) |

= 170 nts

Legend
- BsmBI restriction enzyme cut site
- various guides (20nt)
- SapI restriction enzyme cut site
- various donor sequences (80nt)
- ← Forward and reverse primers

Fig. 1

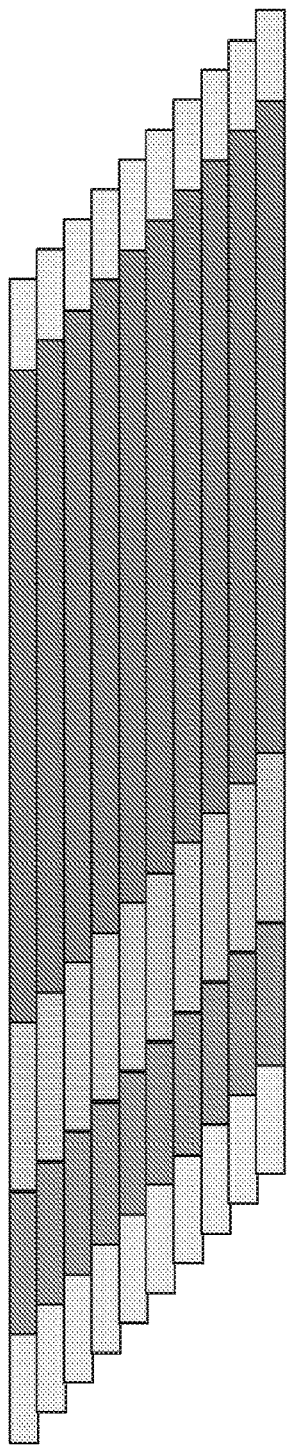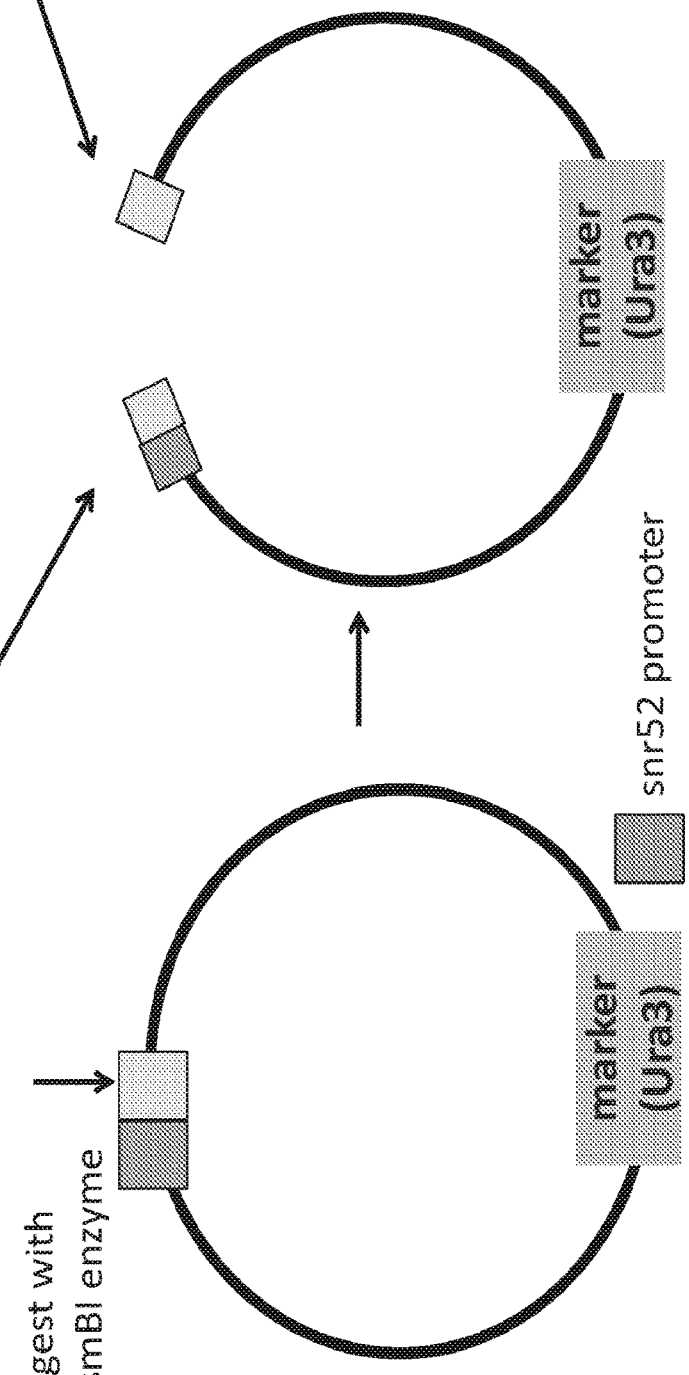
Fig. 2

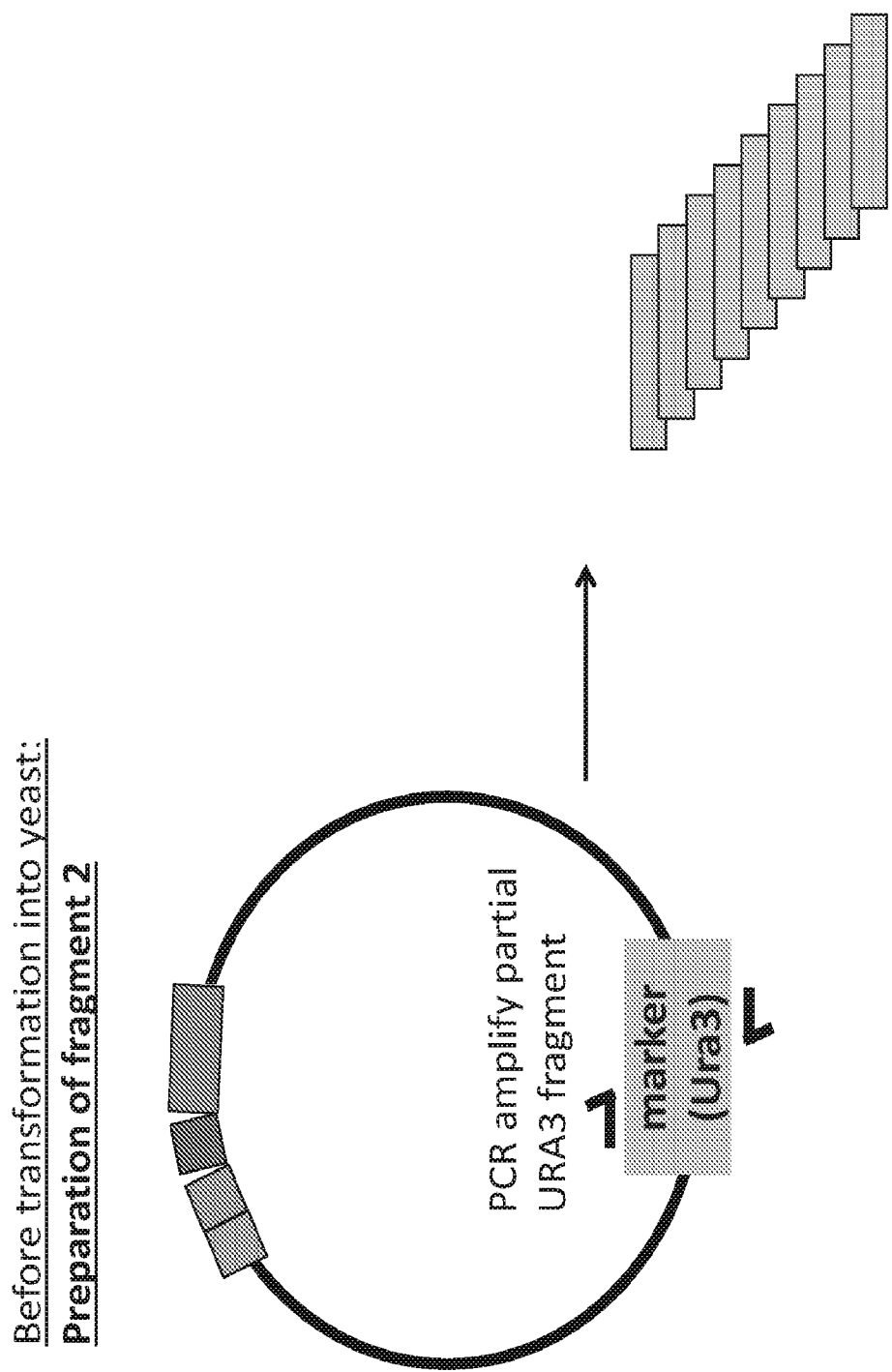

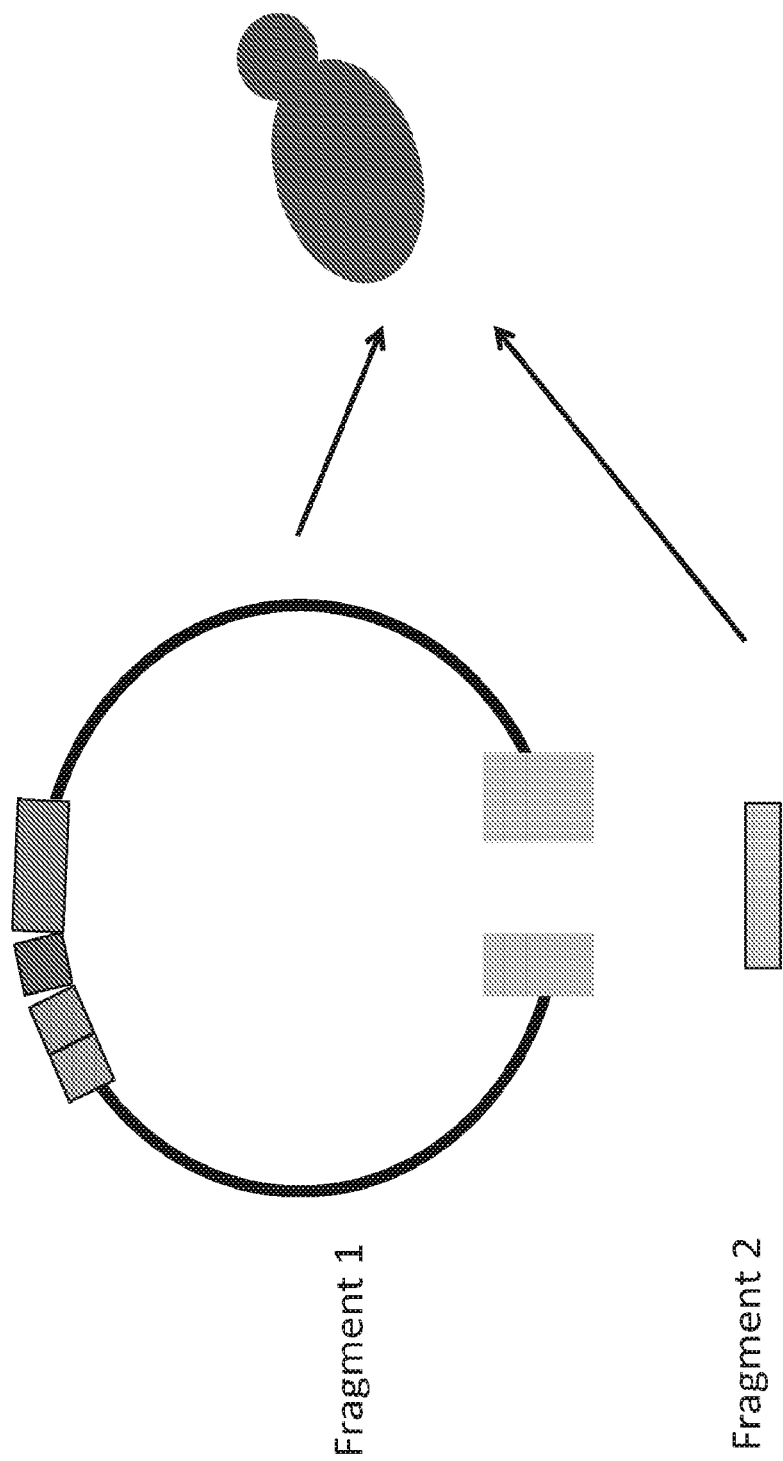

SEQUENCE LISTING

```
<160> NUMBER OF SEQ ID NOS: 49

<210> SEQ ID NO 1
<211> LENGTH: 449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
cgtttgaagt acaactctag attttgtagt gccctcttgg gctagcggta aaggtgcgca      60 tttttttcaca ccctacaatg ttctgttcaa aagattttgg tcaaacgctg tagaagtgaa   120
agttggtgcg catgtttcgg cgttcgaaac ttctccgcag tgaaagataa atgatcaaaa    180
agtcaaaatt aaacaagttt tagagctaga aatagcaagt taaaataagg ctagtccgtt    240
atcaacttga aaaagtggca ccgagtcggt ggtgcttttt ttgtttttta tgtcttcggt    300
gaagaatgaa cctgcatcaa gtcaaatgga tatattttct cagagtggag ggggcagcta    360
gcactttcat gcctgactac gtcaactatt ggaggcggtt tatggtaccc aattcgccct    420
atagtgagtc gtattacgcg cgctcactg                                      449

<210> SEQ ID NO 2
<211> LENGTH: 10756
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gcttccacaa acattgctca aaagtatctc tttgctatat atctctgtgc tatatcccta     60
tataacctac ccatccacct ttcgctcctt gaacttgcat ctaaactcga cctctacatt    120
ttttatgttt atctctagta ttactcttta gacaaaaaaa ttgtagtaag aactattcat    180
agagtgaatc gaaaacaata cgaaaatgta aacatttcct atacgtagta tatagagaca    240
aaatagaaga aaccgttcat aattttctga ccaatgaaga atcatcaacg ctatcacttt    300
ctgttcacaa agtatgcgca atccacatcg gtatagaata taatcgggga tgcctttatc    360
ttgaaaaaat gcacccgcag cttcgctagt aatcagtaaa cgcgggaagt ggagtcaggc    420 ttttttttatg gaagagaaaa tagacaccaa agtagccttc ttctaacctt aacggaccta    480
cagtgcaaaa agttatcaag agactgcatt atagagcgca caaggagaa aaaaagtaat     540 ctaagatgct ttgttagaaa aatagcgctc tcgggatgca tttttgtaga acaaaaaaga    600
agtatagatt ctttgttggt aaaatagcgc tctcgcgttg catttctgtt ctgtaaaaat    660
gcagctcaga ttctttgttt gaaaaattag cgctctcgcg ttgcattttt gttttacaaa    720
aatgaagcac agattcttcg ttggtaaaat agcgctttcg cgttgcattt ctgttctgta    780
aaaatgcagc tcagattctt tgtttgaaaa attagcgctc tcgcgttgca ttttgttct    840 acaaaatgaa gcacagatgc ttcgttcagg tggcactttt cggggaaatg tgcgcggaac    900
```

```
ccctatttgt ttatttttct aaatacattc aaatatgtat ccgctcatga gacaataacc      960
ctgataaatg cttcaataat attgaaaaag gaagagtatg agtattcaac atttccgtgt     1020
cgcccttatt cccttttttg cggcattttg ccttcctgtt tttgctcacc cagaaacgct     1080
ggtgaaagta aaagatgctg aagatcagtt gggtgcacga gtgggttaca tcgaactgga     1140
tctcaacagc ggtaagatcc ttgagagttt tcgccccgaa gaacgttttc caatgatgag     1200 cactttttaaa gttctgctat gtggcgcggt attatcccgt attgacgccg ggcaagagca     1260
actcggtcgc cgcatacact attctcagaa tgacttggtt gagtactcac cagtcacaga     1320
aaagcatctt acggatggca tgacagtaag agaattatgc agtgctgcca taaccatgag     1380
tgataacact gcggccaact tacttctgac aacgatcgga ggaccgaagg agctaaccgc     1440
ttttttgcac aacatggggg atcatgtaac tcgccttgat cgttgggaac cggagctgaa     1500
tgaagccata ccaaacgacg agcgtgacac cacgatgcct gtagcaatgg caacaacgtt     1560
gcgcaaacta ttaactggcg aactacttac tctagcttcc cggcaacaat taatagactg     1620
gatggaggcg gataaagttg caggaccact tctgcgctcg gcccttccgg ctggctggtt     1680
tattgctgat aaatctggag ccggtgagcg tgggtctcgc ggtatcattg cagcactggg     1740
gccagatggt aagccctccc gtatcgtagt tatctacacg acggggagtc aggcaactat     1800
ggatgaacga aatagacaga tcgctgagat aggtgcctca ctgattaagc attggtaact     1860
gtcagaccaa gtttactcat atatacttta gattgattta aaacttcatt tttaatttaa     1920
aaggatctag gtgaagatcc ttttttgataa tctcatgacc aaaatccctt aacgtgagtt     1980
ttcgttccac tgagcgtcag accccgtaga aaagatcaaa ggatcttctt gagatccttt     2040
ttttctgcgc gtaatctgct gcttgcaaac aaaaaaacca ccgctaccag cggtggtttg     2100
tttgccggat caagagctac caactctttt tccgaaggta actggcttca gcagagcgca     2160
gataccaaat actgtccttc tagtgtagcc gtagttaggc caccacttca agaactctgt     2220
agcaccgcct acatacctcg ctctgctaat cctgttacca gtggctgctg ccagtggcga     2280
taagtcgtgt cttaccgggt tggactcaag acgatagtta ccggataagg cgcagcggtc     2340
gggctgaacg gggggttcgt gcacacagcc cagcttggag cgaacgacct acaccgaact     2400
gagataccta cagcgtgagc tatgagaaag cgccacgctt cccgaaggga gaaaggcgga     2460
caggtatccg gtaagcggca gggtcggaac aggagagcgc acgagggagc ttccaggggg     2520
aaacgcctgg tatctttata gtcctgtcgg gtttcgccac ctctgacttg agcgtcgatt     2580
tttgtgatgc tcgtcagggg ggcggagcct atggaaaaac gccagcaacg cggccttttt     2640
acggttcctg gccttttgct ggccttttgc tcacatgttc tttcctgcgt tatccctga      2700 ttctgtggat aaccgtatta ccgcctttga gtgagctgat accgctcgcc gcagccgaac     2760
gaccgagcgc agcgagtcag tgagcgagga agcgaaagag cgcccaatac gcaaaccgcc     2820
tctccccgcg cgttggccga ttcattaatg cagctggcac gacaggtttc ccgactggaa     2880
agcgggcagt gagcgcaacg caattaatgt gagttacctc actcattagg caccccaggc     2940
tttacacttt atgcttccgg ctcctatgtt gtgtggaatt gtgagcggat aacaatttca     3000
cacaggaaac agctatgacc atgattacgc caagcgcgca attaaccctc actaaaggga     3060
acaaaagctg gagctcactt ctttgaaaag ataatgtatg attatgcttt cactcatatt     3120
tatacagaaa cttgatgttt ctttcgagt  atatacaagg tgattacatg tacgtttgaa     3180
gtacaactct agattttgta gtgccctctt gggctagcgg taaaggtgcg cattttttca     3240
```

```
cacccctacaa tgttctgttc aaaagatttt ggtcaaacgc tgtagaagtg aaagttggtg    3300
cgcatgtttc ggcgttcgaa acttctccgc agtgaaagat aaatgatccg agacgattaa    3360
tgcgtctcga catggtaccc aattcgccct atagtgagtc gtattacgcg cgctcactgg    3420
ccgtcgtttt acaacgtcgt gactgggaaa accctggcgt tacccaactt aatcgccttg    3480
cagcacatcc cccttttcgcc agctggcgta atagcgaaga ggcccgcacc gatcgccctt    3540
cccaacagtt gcgcagcctg aatggcgaat ggacgcgccc tgtagcggcg cattaagcgc    3600
ggcgggtgtg gtggttacgc gcagcgtgac cgctacactt gccagcgccc tagcgcccgc    3660
tcctttcgct ttcttccctt cctttctcgc cacgttcgcc ggctttcccc gtcaagctct    3720
aaatcggggg ctccctttag ggttccgatt tagtgcttta cggcacctcg accccaaaaa    3780
acttgattag ggtgatggtt cacgtagtgg gccatcgccc tgatagacgg ttttttcgccc    3840 tttgacgttg gagtccacgt tctttaatag tggactcttg ttccaaactg gaacaacact    3900 caacccctatc tcggtctatt cttttgattt ataagggatt ttgccgattt cggcctattg    3960
gttaaaaaat gagctgattt aacaaaaatt taacgcgaat tttaacaaaa tattaacgtt    4020
tacaatttcc tgatgcggta ttttctcctt acgcatctgt gcggtatttc acaccgcata    4080
gggtaataac tgatataatt aaattgaagc tctaatttgt gagtttagta tacatgcatt    4140
tacttataat acagttttt agttttgctg gccgcatctt ctcaaatatg cttcccagcc    4200
tgcttttctg taacgttcac cctctacctt agcatccctt cccttttgcaa atagtcctct    4260 tccaacaata ataatgtcag atcctgtaga gaccacatca tccacggttc tatactgttg    4320
acccaatgcg tcccccttgt catctaaacc cacaccgggt gtcataatca accaatcgta    4380
accttcatct cttccaccca tgtctcttg agcaataaag ccgataacaa atctttgtc    4440 gctcttagca atgtcaacag tacccttagt atattctcca gtagataggg agcccttgca    4500
tgacaattct gctaacatca aaaggcctct aggttccttt gttacttctt ctgccgcctg    4560
cttcaaaccg ctaacaatac ctgggcccac cacaccgtgt gcattcgtaa tgtctgccca    4620
ttctgctatt ctgtatacac ccgcagagta ctgcaatttg actgtattac caatgtcagc    4680
aaattttctg tcttcgaaga gtaaaaaatt gtacttggcg gataatgcct ttagcggctt    4740
aactgtgccc tccatggaaa aatcagtcaa gatatccaca tgtgttttta gtaaacaaat    4800
tttgggacct aatgcttcaa ctaactccag taattccttg gtggtacgaa catccaatga    4860
agcacacaag tttgtttgct tttcgtgcat gatattaaat agcttggcag caacaggact    4920
aggatgagta gcagcacgtt ccttatatgt agctttcgac atgatttatc ttcgtttcct    4980
gcaggttttt gttctgtgca gttgggttaa gaatactggg caatttcatg tttcttcaac    5040
actacatatg cgtatatata ccaatctaag tctgtgctcc ttccttcgtt cttccttctg    5100
ttcggagatt accgaatcaa aaaatttca agaaaccga aatcaaaaaa aagaataaaa    5160
aaaaaatgat gaattgaatt gaaaagctgt ggtatggtgc actctcagta caatctgctc    5220
tgatgccgca tagttaagcc agccccgaca cccgccaaca cccgctgacg cgccctgacg    5280
ggcttgtctg ctcccggcat ccgcttacag acaagctgtg acggtctccg ggagctgcat    5340
gtgtcagagg ttttcaccgt catcaccgaa acgcgcgagc ttcacaaac attgctcaaa    5400 agtatctctt tgctatatat ctctgtgcta tatccctata aacctacccc atccaccttt    5460
cgctccttga acttgcatct aaactcgacc tctacatttt ttatgtttat ctctagtatt    5520
actctttaga caaaaaaatt gtagtaagaa ctattcatag agtgaatcga aaacaatacg    5580
aaaatgtaaa catttcctat acgtagtata tagagacaaa atagaagaaa ccgttcataa    5640
```

```
ttttctgacc aatgaagaat catcaacgct atcactttct gttcacaaag tatgcgcaat    5700
ccacatcggt atagaatata atcggggatg cctttatctt gaaaaaatgc acccgcagct    5760
tcgctagtaa tcagtaaacg cgggaagtgg agtcaggctt ttttatgga agagaaaata    5820 gacaccaaag tagccttctt ctaaccttaa cggacctaca gtgcaaaaag ttatcaagag    5880
actgcattat agagcgcaca aaggagaaaa aaagtaatct aagatgcttt gttagaaaaa    5940
tagcgctctc gggatgcatt tttgtagaac aaaaaagaag tatagattct ttgttggtaa    6000
aatagcgctc tcgcgttgca tttctgttct gtaaaaatgc agctcagatt ctttgtttga    6060
aaaattagcg ctctcgcgtt gcattttgt tttacaaaaa tgaagcacag attcttcgtt     6120
ggtaaaatag cgctttcgcg ttgcatttct gttctgtaaa aatgcagctc agattctttg    6180
tttgaaaaat tagcgctctc gcgttgcatt tttgttctac aaaatgaagc acagatgctt    6240
cgttcaggtg gcactttcg gggaaatgtg cgcggaaccc ctatttgttt atttttctaa     6300
atacattcaa atatgtatcc gctcatgaga caataaccct gataaatgct tcaataatat    6360
tgaaaaagga agagtatgag tattcaacat ttccgtgtcg cccttattcc cttttttgcg    6420 gcatttgcc ttcctgtttt tgctcaccca gaaacgctgg tgaaagtaaa agatgctgaa     6480
gatcagttgg gtgcacgagt gggttacatc gaactggatc tcaacagcgg taagatcctt    6540
gagagttttc gccccgaaga cgttttcca atgatgagca cttttaaagt tctgctatgt     6600
ggcgcggtat tatcccgtat tgacgccggg caagagcaac tcggtcgccg catacactat    6660
tctcagaatg acttggttga gtactcacca gtcacagaaa agcatcttac ggatggcatg    6720
acagtaagag aattatgcag tgctgccata accatgagtg ataacactgc ggccaactta    6780
cttctgacaa cgatcggagg accgaaggag ctaaccgctt ttttgcacaa catgggggat    6840
catgtaactc gccttgatcg ttgggaaccg gagctgaatg aagccatacc aaacgacgag    6900
cgtgacacca cgatgcctgt agcaatggca acaacgttgc gcaaactatt aactggcgaa    6960
ctacttactc tagcttcccg gcaacaatta atagactgga tggaggcgga taaagttgca    7020
ggaccacttc tgcgctcggc ccttccggct ggctggttta ttgctgataa atctggagcc    7080
ggtgagcgtg ggtctcgcgg tatcattgca gcactggggc cagatggtaa gccctcccgt    7140
atcgtagtta tctacacgac ggggagtcag gcaactatgg atgaacgaaa tagacagatc    7200
gctgagatag gtgcctcact gattaagcat tggtaactgt cagaccaagt ttactcatat    7260
atactttaga ttgatttaaa acttcatttt taatttaaaa ggatctaggt gaagatcctt    7320
tttgataatc tcatgaccaa aatcccttaa cgtgagtttt cgttccactg agcgtcagac    7380
cccgtagaaa agatcaaagg atcttcttga gatcctttt ttctgcgcgt aatctgctgc     7440
ttgcaaacaa aaaaccacc gctaccagcg gtggtttgtt tgccggatca agagctacca    7500
actctttttc cgaaggtaac tggcttcagc agagcgcaga taccaaatac tgtccttcta    7560
gtgtagccgt agttaggcca ccacttcaag aactctgtag caccgcctac atacctcgct    7620
ctgctaatcc tgttaccagt ggctgctgcc agtggcgata agtcgtgtct taccgggttg    7680
gactcaagac gatagttacc ggataaggcg cagcggtcgg gctgaacggg gggttcgtgc    7740
acacagccca gcttggagcg aacgacctac accgaactga gatacctaca gcgtgagcta    7800
tgagaaagcg ccacgcttcc cgaagggaga aaggcggaca ggtatccggt aagcggcagg    7860
gtcggaacag gagagcgcac gagggagctt ccagggggaa acgcctggta tctttatagt    7920
cctgtcgggt ttcgccacct ctgacttgag cgtcgatttt tgtgatgctc gtcagggggg    7980
```

```
cggagcctat ggaaaaacgc cagcaacgcg gccttttac  ggttcctggc cttttgctgg   8040
ccttttgctc acatgttctt tcctgcgtta tccctgatt  ctgtggataa ccgtattacc   8100
gcctttgagt gagctgatac cgctcgccgc agccgaacga ccgagcgcag cgagtcagtg   8160
agcgaggaag cgaaagagcg cccaatacgc aaaccgcctc tccccgcgcg ttggccgatt   8220
cattaatgca gctggcacga caggtttccc gactggaaag cgggcagtga gcgcaacgca   8280
attaatgtga gttacctcac tcattaggca ccccaggctt tacactttat gcttccggct   8340
cctatgttgt gtggaattgt gagcggataa caatttcaca caggaaacag ctatgaccat   8400
gattacgcca agcgcgcaat taaccctcac taaagggaac aaaagctgga gctcacttct   8460
ttgaaaagat aatgtatgat tatgctttca ctcatattta tacagaaact tgatgttttc   8520
tttcgagtat atacaaggtg attacatgta cgtttgaagt acaactctag attttgtagt   8580
gccctcttgg gctagcggta aaggtgcgca ttttttcaca ccctacaatg ttctgttcaa   8640
aagattttgg tcaaacgctg tagaagtgaa agttggtgcg catgtttcgg cgttcgaaac   8700
ttctccgcag tgaaagataa atgatccgag acgattaatg cgtctcgaca tggtacccaa   8760
ttcgccctat agtgagtcgt attacgcgcg ctcactggcc gtcgttttac aacgtcgtga   8820
ctgggaaaac cctggcgtta cccaacttaa tcgccttgca gcacatcccc ctttcgccag   8880
ctggcgtaat agcgaagagg cccgcaccga tcgcccttcc caacagttgc gcagcctgaa   8940
tggcgaatgg acgcgccctg tagcggcgca ttaagcgcgg cgggtgtggt ggttacgcgc   9000
agcgtgaccg ctacacttgc cagcgcccta gcgcccgctc ctttcgcttt cttcccttcc   9060
tttctcgcca cgttcgccgg ctttccccgt caagctctaa atcgggggct ccctttaggg   9120
ttccgattta gtgctttacg gcacctcgac cccaaaaaac ttgattaggg tgatggttca   9180
cgtagtgggc catcgccctg atagacggtt tttcgccctt tgacgttgga gtccacgttc   9240
tttaatagtg gactcttgtt ccaaactgga acaacactca accctatctc ggtctattct   9300
tttgatttat aagggatttt gccgatttcg gcctattggt taaaaaatga gctgatttaa   9360
caaaaattta acgcgaattt taacaaaata ttaacgttta caatttcctg atgcggtatt   9420
ttctccttac gcatctgtgc ggtatttcac accgcatagg gtaataactg atataattaa   9480
attgaagctc taatttgtga gtttagtata catgcattta cttataatac agttttttag   9540
ttttgctggc cgcatcttct caaatatgct tcccagcctg cttttctgta acgttcaccc   9600
tctaccttag catcccttcc ctttgcaaat agtcctcttc aacaataat  aatgtcagat   9660
cctgtagaga ccacatcatc cacggttcta tactgttgac ccaatgcgtc ccccttgtca   9720
tctaaaccca caccgggtgt cataatcaac caatcgtaac cttcatctct tccacccatg   9780
tctctttgag caataaagcc gataacaaaa tctttgtcgc tcttagcaat gtcaacagta   9840
cccttagtat attctccagt agataggga  cccttgcatg acaattctgc taacatcaaa   9900
aggcctctag gttcctttgt tacttcttct gccgcctgct tcaaaccgct aacaatacct   9960
gggcccacca caccgtgtgc attcgtaatg tctgcccatt ctgctattct gtatacaccc  10020
gcagagtact gcaatttgac tgtattacca atgtcagcaa attttctgtc ttcgaagagt  10080
aaaaaattgt acttggcgga taatgccttt agcggcttaa ctgtgccctc catgaaaaa   10140
tcagtcaaga tatccacatg tgtttttagt aaacaaattt gggacctaa  tgcttcaact  10200
aactccagta attccttggt ggtacgaaca tccaatgaag cacacaagtt tgtttgcttt  10260
tcgtgcatga tattaaatag cttggcagca acaggactag gatgagtagc agcacgttcc  10320
ttatatgtag ctttcgacat gatttatctt cgtttcctgc aggttttgt  tctgtgcagt  10380
```

```
tgggttaaga atactgggca atttcatgtt tcttcaacac tacatatgcg tatatatacc    10440
aatctaagtc tgtgctcctt ccttcgttct tccttctgtt cggagattac cgaatcaaaa    10500
aaatttcaaa gaaaccgaaa tcaaaaaaaa gaataaaaaa aaaatgatga attgaattga    10560
aaagctgtgg tatggtgcac tctcagtaca atctgctctg atgccgcata gttaagccag    10620
ccccgacacc cgccaacacc cgctgacgcg ccctgacggg cttgtctgct cccggcatcc    10680
gcttacagac aagctgtgac ggtctccggg agctgcatgt gtcagaggtt ttcaccgtca    10740
tcaccgaaac gcgcga                                                    10756

<210> SEQ ID NO 3
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tttgaagtac aactctagat tttgtagtgc cctcttgggc tagcggtaaa ggtgcgcatt     60
ttttcacacc ctacaatgtt ctgttcaaaa gattttggtc aaacgctgta gaagtgaaag    120
ttggtgcgca tgtttcggcg ttcgaaactt ctccgcagtg aaagataaat gatcacttga    180
agattcttta gtgtgtttta gagctagaaa tagcaagtta aaataaggct agtccgttat    240
caacttgaaa aagtggcacc gagtcggtgg tgcttttttt gttttttatg tctaatgtga    300
tgtgctaacg attgagattg agcatgttga tgttcctaaa gaatcttcaa gtaaaacatc    360
ccaaattaaa aatttaccct tctggtaccc aattcgccct atagtgagtc gtattacgcg    420
cgctcactgt ttgaagtaca actctagatt ttgtagtgcc ctcttgggct agcggtaaag    480
gtgcgcattt tttcacaccc tacaatgttc tgttcaaaag attttggtca aacgctgtag    540
aagtgaaagt tggtgcgcat gtttcggcgt tcgaaacttc tccgcagtga agataaatg     600 atcacttgaa gattctttag tgtgttttag agctagaaat agcaagttaa ataaggcta     660 gtccgttatc aacttgaaaa agtggcaccg agtcggtggt gctttttttg ttttttatgt    720
ctaatgtgat gtgctaacga ttgagattga gcatgttgat gttcctaaag aatcttcaag    780
taaaacatcc caaattaaaa atttaccctt ctggtaccca attcgcccta tagtgagtcg    840
tattacgcgc gctcactg                                                  858

<210> SEQ ID NO 4
<211> LENGTH: 862
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cgtttgaagt acaactctag attttgtagt gccctcttgg gctagcggta aggtgcgca     60 ttttttcaca ccctacaatg ttctgttcaa aagattttgg tcaaacgctg tagaagtgaa    120
agttggtgcg catgtttcgg cgttcgaaac ttctccgcag tgaaagataa atgatcactt    180
gaagattctt tagtgtgttt tagagctaga aatagcaagt taaaataagg ctagtccgtt    240
atcaacttga aaagtggca ccgagtcggt ggtgcttttt ttgttttttta tgtctaatgt    300 gatgtgctaa cgattgagat tgagcatgtt gatgttccta cttcaagtaa aacatcccaa    360
```

| | |
|---|---|
| attaaaaatt taccottctc cagaaggtac ccaattcgcc ctatagtgag tcgtattacg | 420 |
| cgcgctcact gcgtttgaag tacaactcta gattttgtag tgccctcttg gctagcggt | 480 |
| aaaggtgcgc attttttcac acctacaat gttctgttca aagatttg gtcaaacgct | 540 |
| gtagaagtga agttggtgc gcatgtttcg gcgttcgaaa cttctccgca gtgaaagata | 600 |
| aatgatcact tgaagattct ttagtgtgtt ttagagctag aaatagcaag ttaaaataag | 660 |
| gctagtccgt tatcaacttg aaaaagtggc accgagtcgg tggtgctttt tttgttttt | 720 |
| atgtctaatg tgatgtgcta acgattgaga ttgagcatgt tgatgttcct acttcaagta | 780 |
| aaacatccca aattaaaaat ttaccottct ccagaaggta cccaattcgc cctatagtga | 840 |
| gtcgtattac gcgcgctcac tg | 862 |

<210> SEQ ID NO 5
<211> LENGTH: 862
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 5

| | |
|---|---|
| cgtttgaagt acaactctag attttgtagt gccctcttgg gctagcggta aaggtgcgca | 60 |
| ttttttcaca ccctacaatg ttctgttcaa aagattttgg tcaaacgctg tagaagtgaa | 120 |
| agttggtgcg catgtttcgg cgttcgaaac ttctccgcag tgaaagataa atgatcactt | 180 |
| gaagattctt tagtgtgttt tagagctaga aatagcaagt taaataagg ctagtccgtt | 240 |
| atcaacttga aaaagtggca ccgagtcggt ggtgcttttt ttgttttta tgtctctagc | 300 |
| tgaaaaatgt gatgtgctaa cgattgagat tgagcatgtt aacatcccaa attaaaaatt | 360 |
| taccottctc cagaaacaat cagatggtac ccaattcgcc ctatagtgag tcgtattacg | 420 |
| cgcgctcact gcgtttgaag tacaactcta gattttgtag tgccctcttg gctagcggt | 480 |
| aaaggtgcgc attttttcac acctacaat gttctgttca aagatttg gtcaaacgct | 540 |
| gtagaagtga agttggtgc gcatgtttcg gcgttcgaaa cttctccgca gtgaaagata | 600 |
| aatgatcact tgaagattct ttagtgtgtt ttagagctag aaatagcaag ttaaaataag | 660 |
| gctagtccgt tatcaacttg aaaaagtggc accgagtcgg tggtgctttt tttgttttt | 720 |
| atgtctctag ctgaaaaatg tgatgtgcta acgattgaga ttgagcatgt taacatccca | 780 |
| aattaaaaat ttaccottct ccagaaacaa tcagatggta cccaattcgc cctatagtga | 840 |
| gtcgtattac gcgcgctcac tg | 862 |

<210> SEQ ID NO 6
<211> LENGTH: 862
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 6

| | |
|---|---|
| cgtttgaagt acaactctag attttgtagt gccctcttgg gctagcggta aaggtgcgca | 60 |
| ttttttcaca ccctacaatg ttctgttcaa aagattttgg tcaaacgctg tagaagtgaa | 120 |
| agttggtgcg catgtttcgg cgttcgaaac ttctccgcag tgaaagataa atgatcactt | 180 |
| gaagattctt tagtgtgttt tagagctaga aatagcaagt taaataagg ctagtccgtt | 240 |
| atcaacttga aaaagtggca ccgagtcggt ggtgcttttt ttgttttta tgtctatatc | 300 |

```
gaaaaactag ctgaaaaatg tgatgtgcta acgattgaga ttacccttct ccagaaacaa    360
tcagattgat acaagacaaa tatatggtac ccaattcgcc ctatagtgag tcgtattacg    420
cgcgctcact gcgtttgaag tacaactcta gattttgtag tgccctcttg ggctagcggt    480
aaaggtgcgc attttttcac acccctacaat gttctgttca aaagattttg gtcaaacgct    540
gtagaagtga agttggtgc gcatgtttcg gcgttcgaaa cttctccgca gtgaaagata    600
aatgatcact tgaagattct ttagtgtgtt ttagagctag aaatagcaag ttaaaataag    660
gctagtccgt tatcaacttg aaaaagtggc accgagtcgg tggtgctttt tttgtttttt    720
atgtctatat cgaaaaacta gctgaaaaat gtgatgtgct aacgattgag attacccttc    780
tccagaaaca atcagattga tacaagacaa atatatggta cccaattcgc cctatagtga    840
gtcgtattac gcgcgctcac tg                                              862

<210> SEQ ID NO 7
<211> LENGTH: 862
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
cgtttgaagt acaactctag attttgtagt gccctcttgg gctagcggta aaggtgcgca     60
ttttttcaca ccctacaatg ttctgttcaa aagattttgg tcaaacgctg tagaagtgaa    120
agttggtgcg catgtttcgg cgttcgaaac ttctccgcag tgaaagataa atgatcactt    180
gaagattctt tagtgtgttt tagagctaga aatagcaagt taaaataagg ctagtccgtt    240
atcaacttga aaaagtggca ccgagtcggt ggtgcttttt ttgttttta tgtctcacgt    300 taatggctcc ttttccaatc ctcttgatat cgaaaaacta tacaagacaa atatattcaa    360
aaagagcatt taatcaaaaa tggtaggtac ccaattcgcc ctatagtgag tcgtattacg    420
cgcgctcact gcgtttgaag tacaactcta gattttgtag tgccctcttg ggctagcggt    480
aaaggtgcgc attttttcac acccctacaat gttctgttca aaagattttg gtcaaacgct    540
gtagaagtga agttggtgc gcatgtttcg gcgttcgaaa cttctccgca gtgaaagata    600
aatgatcact tgaagattct ttagtgtgtt ttagagctag aaatagcaag ttaaaataag    660
gctagtccgt tatcaacttg aaaaagtggc accgagtcgg tggtgctttt tttgtttttt    720
atgtctcacg ttaatggctc cttttccaat cctcttgata tcgaaaaact atacaagaca    780
aatatattca aaaagagcat ttaatcaaaa tggtaggta cccaattcgc cctatagtga    840
gtcgtattac gcgcgctcac tg                                              862

<210> SEQ ID NO 8
<211> LENGTH: 862
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cgtttgaagt acaactctag attttgtagt gccctcttgg gctagcggta aaggtgcgca     60
ttttttcaca ccctacaatg ttctgttcaa aagattttgg tcaaacgctg tagaagtgaa    120
agttggtgcg catgtttcgg cgttcgaaac ttctccgcag tgaaagataa atgatcactt    180
```

```
gaagattctt tagtgtgttt tagagctaga aatagcaagt taaaataagg ctagtccgtt    240
atcaacttga aaaagtggca ccgagtcggt ggtgctttt ttgtttttta tgtctaagac    300
ggtaatacta gatgctgaaa attctcctgc caaacaaata gtgttcctgt ggaacaagcc    360
agtgagacgt ccctattgaa tgttgggtac ccaattcgcc ctatagtgag tcgtattacg    420
cgcgctcact gcgtttgaag tacaactcta gattttgtag tgccctcttg ggctagcggt    480
aaaggtgcgc attttttcac acctacaat gttctgttca aaagattttg gtcaaacgct    540
gtagaagtga agttggtgc gcatgtttcg gcgttcgaaa cttctccgca gtgaaagata    600
aatgatcact tgaagattct ttagtgtgtt ttagagctag aaatagcaag ttaaaataag    660
gctagtccgt tatcaacttg aaaaagtggc accgagtcgg tggtgctttt tttgttttt    720 atgtctaaga cggtaatact agatgctgaa aattctcctg ccaaacaaat agtgttcctg    780
tggaacaagc cagtgagacg tccctattga atgttgggta cccaattcgc ctatagtga    840 gtcgtattac gcgcgctcac tg                                             862
```

<210> SEQ ID NO 9
<211> LENGTH: 868
<212> TYPE: DNA
<213> ORGANISM: Artificial Sequence
<220> FEATURE:
<223> OTHER INFORMATION: Description of Artificial Sequence: Synthetic
    polynucleotide <400> SEQUENCE: 9

```
cgtttgaagt acaactctag attttgtagt gccctcttgg gctagcggta aaggtgcgca     60
ttttttcaca ccctacaatg ttctgttcaa aagattttgg tcaaacgctg tagaagtgaa    120
agttggtgcg catgtttcgg cgttcgaaac ttctccgcag tgaaagataa atgatctttg    180
ttcttatgcc aacagggttt tagagctaga aatagcaagt taaaataagg ctagtccgtt    240
atcaacttga aaaagtggca ccgagtcggt ggtgctttt ttgtttttta tgtcttcgct    300
gcctggtttt agacctaacc aactagaggc tgtaaatgca actcaacttc ctgcagtggt    360
gaaatcgggt aaaacacatg gtactactgg tacccaattc gccctatagt gagtcgtatt    420
acgcgcgctc actgcgtttg aagtacaact ctagattttg tagtgccctc ttgggctagc    480
ggtaaaggtg cgcattttt cacacctac aatgttctgt tcaaaagatt ttggtcaaac    540
gctgtagaag tgaaagttgg tgcgcatgtt tcggcgttcg aaacttctcc gcagtgaaag    600
ataaatgatc tttgttctta tgccaacagg gttttagagc tagaaatagc aagttaaaat    660
aaggctagtc cgttatcaac ttgaaaaagt ggcaccgagt cggtggtgct tttttgttt    720 tttatgtctt cgctgcctgg ttttagacct aaccaactag aggctgtaaa tgcaactcaa    780
cttcctgcag tggtgaaatc gggtaaaaca catggtacta ctggtaccca attcgcccta    840
tagtgagtcg tattacgcgc gctcactg                                        868
```

<210> SEQ ID NO 10
<211> LENGTH: 868
<212> TYPE: DNA
<213> ORGANISM: Artificial Sequence
<220> FEATURE:
<223> OTHER INFORMATION: Description of Artificial Sequence: Synthetic
    polynucleotide <400> SEQUENCE: 10

```
cgtttgaagt acaactctag attttgtagt gccctcttgg gctagcggta aaggtgcgca     60
ttttttcaca ccctacaatg ttctgttcaa aagattttgg tcaaacgctg tagaagtgaa    120
```

```
agttggtgcg catgtttcgg cgttcgaaac ttctccgcag tgaaagataa atgatcttta      180
aatttaggaa atagaagttt tagagctaga aatagcaagt taaaataagg ctagtccgtt      240
atcaacttga aaaagtggca ccgagtcggt ggtgcttttt ttgttttttta tgtcttcgtt     300 acgctcgaca caagaactta ataatctgcg aatgacatac gaaatgcctg acagtatttt     360
aaaaaagatg gcagcaatat taccaatggg tacccaattc gccctatagt gagtcgtatt     420
acgcgcgctc actgcgtttg aagtacaact ctagattttg tagtgccctc ttgggctagc     480
ggtaaaggtg cgcattttt cacaccctac aatgttctgt tcaaaagatt ttggtcaaac      540
gctgtagaag tgaaagttgg tgcgcatgtt tcggcgttcg aaacttctcc gcagtgaaag    600
ataaatgatc tttaaattta ggaaatagaa gttttagagc tagaaatagc aagttaaaat     660
aaggctagtc cgttatcaac ttgaaaaagt ggcaccgagt cggtggtgct tttttttgttt   720 tttatgtctt cgttacgctc gacacaagaa cttaataatc tgcgaatgac atacgaaatg    780
cctgacagta ttttaaaaaa gatggcagca atattaccaa tgggtaccca attcgcccta     840
tagtgagtcg tattacgcgc gctcactg                                        868
```

<210> SEQ ID NO 11
<211> LENGTH: 868
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
cgtttgaagt acaactctag attttgtagt gccctcttgg gctagcggta aggtgcgca      60 tttttcaca ccctacaatg ttctgttcaa aagattttgg tcaaacgctg tagaagtgaa     120
agttggtgcg catgtttcgg cgttcgaaac ttctccgcag tgaaagataa atgatctttg    180
ttcttatgcc aacagggttt tagagctaga aatagcaagt taaaataagg ctagtccgtt    240
atcaacttga aaaagtggca ccgagtcggt ggtgcttttt ttgttttttta tgtcttcgaa   300 atgcaacttt gcaaggtaag gatgttttg ttcttatgcc aacaggggct ggtgcttctc    360
tttgctatca acttcctgca gtggtgaagg tacccaattc gccctatagt gagtcgtatt    420
acgcgcgctc actgcgtttg aagtacaact ctagattttg tagtgccctc ttgggctagc    480
ggtaaaggtg cgcattttt cacaccctac aatgttctgt tcaaaagatt ttggtcaaac    540
gctgtagaag tgaaagttgg tgcgcatgtt tcggcgttcg aaacttctcc gcagtgaaag   600
ataaatgatc tttgttctta tgccaacagg gttttagagc tagaaatagc aagttaaaat   660
aaggctagtc cgttatcaac ttgaaaaagt ggcaccgagt cggtggtgct tttttttgttt   720 tttatgtctt cgaaatgcaa ctttgcaagg taaggatgtt tttgttctta tgccaacagg   780
ggctggtgct tctctttgct atcaacttcc tgcagtggtg aaggtaccca attcgcccta   840
tagtgagtcg tattacgcgc gctcactg                                       868
```

<210> SEQ ID NO 12
<211> LENGTH: 868
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
cgtttgaagt acaactctag attttgtagt gccctcttgg gctagcggta aaggtgcgca        60
ttttttcaca ccctacaatg ttctgttcaa aagattttgg tcaaacgctg tagaagtgaa       120
agttggtgcg catgtttcgg cgttcgaaac ttctccgcag tgaaagataa atgatcttta       180
aatttaggaa atagaagttt tagagctaga aatagcaagt taaaataagg ctagtccgtt       240
atcaacttga aaaagtggca ccgagtcggt ggtgcttttt ttgtttttta tgtcttcgtg       300
acatacgaac gtctgaggga attatcttta aatttaggaa atagataagt tcctccagtt       360
gggaacttta tgcctgacag tattttaagg tacccaattc gccctatagt gagtcgtatt       420
acgcgcgctc actgcgtttg aagtacaact ctagattttg tagtgccctc ttgggctagc       480
ggtaaaggtg cgcatttttt cacaccctac aatgttctgt tcaaaagatt ttggtcaaac       540
gctgtagaag tgaaagttgg tgcgcatgtt tcggcgttcg aaacttctcc gcagtgaaag       600
ataaatgatc tttaaattta ggaaatagaa gttttagagc tagaaatagc aagttaaaat       660
aaggctagtc cgttatcaac ttgaaaaagt ggcaccgagt cggtggtgct ttttttgttt       720
tttatgtctt cgtgacatac gaacgtctga gggaattatc tttaaattta ggaaatagat       780
aagttcctcc agttgggaac tttatgcctg acagtatttt aaggtaccca attcgcccta       840
tagtgagtcg tattacgcgc gctcactg                                          868
```

<210> SEQ ID NO 13
<211> LENGTH: 898
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 13

```
cgtttgaagt acaactctag attttgtagt gccctcttgg gctagcggta aaggtgcgca        60
ttttttcaca ccctacaatg ttctgttcaa aagattttgg tcaaacgctg tagaagtgaa       120
agttggtgcg catgtttcgg cgttcgaaac ttctccgcag tgaaagataa atgatctttg       180
ttcttatgcc aacagggttt tagagctaga aatagcaagt taaaataagg ctagtccgtt       240
atcaacttga aaaagtggca ccgagtcggt ggtgcttttt ttgtttttta tgtcttcgct       300
gcctggtttt agacctaacc aactagaggc tgtaaatgca actagtggag ggggcagcca       360
acttcctgca gtggtgaaat cgggtaaaac acatggtact actggtaccc aattcgccct       420
atagtgagtc gtattacgcg cgctcactgc gtttgaagta caactctaga ttttgtagtg       480
ccctcttggg ctagcggtaa aggtgcgcat ttttcacac cctacaatgt tctgttcaaa       540
agattttggt caaacgctgt agaagtgaaa gttggtgcgc atgtttcggc gttcgaaact       600
tctccgcagt gaaagataaa tgatctttgt tcttatgcca acagggtttt agagctagaa       660
atagcaagtt aaaataaggc tagtccgtta tcaacttgaa aaagtggcac cgagtcggtg       720 gtgcttttt tgtttttat gtcttcgctg cctggtttta gacctaacca actagaggct       780
gtaaatgcaa ctagtggagg gggcagccaa cttcctgcag tggtgaaatc gggtaaaaca       840
catggtacta ctggtaccca attcgcccta tagtgagtcg tattacgcgc gctcactg        898
```

<210> SEQ ID NO 14
<211> LENGTH: 898
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
cgtttgaagt acaactctag attttgtagt gccctcttgg gctagcggta aaggtgcgca      60
ttttttcaca ccctacaatg ttctgttcaa aagattttgg tcaaacgctg tagaagtgaa     120
agttggtgcg catgtttcgg cgttcgaaac ttctccgcag tgaaagataa atgatcttta     180
aatttaggaa atagaagttt tagagctaga aatagcaagt taaaataagg ctagtccgtt     240
atcaacttga aaaagtggca ccgagtcggt ggtgcttttt ttgttttttta tgtcttcgtt     300
acgctcgaca caagaactta ataatctgcg aatgacatac gaaagtggag ggggcagcat     360
gcctgacagt attttaaaaa agatggcagc aatattacca atgggtaccc aattcgccct     420
atagtgagtc gtattacgcg cgctcactgc gtttgaagta caactctaga ttttgtagtg     480
ccctcttggg ctagcggtaa aggtgcgcat tttttcacac cctacaatgt tctgttcaaa     540
agattttggt caaacgctgt agaagtgaaa gttggtgcgc atgtttcggc gttcgaaact     600
tctccgcagt gaaagataaa tgatctttaa atttaggaaa tagaagtttt agagctagaa     660
atagcaagtt aaaataaggc tagtccgtta tcaacttgaa aaagtggcac cgagtcggtg     720
gtgcttttt tgtttttat gtcttcgtta cgctcgacac aagaacttaa taatctgcga     780
atgacatacg aaagtggagg gggcagcatg cctgacagta ttttaaaaaa gatggcagca     840
atattaccaa tgggtaccca attcgcccta tagtgagtcg tattacgcgc gctcactg      898
```

<210> SEQ ID NO 15
<211> LENGTH: 434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
cgtttgaagt acaactctag attttgtagt gccctcttgg gctagcggta aaggtgcgca      60
ttttttcaca ccctacaatg ttctgttcaa aagattttgg tcaaacgctg tagaagtgaa     120
agttggtgcg catgtttcgg cgttcgaaac ttctccgcag tgaaagataa atgatcccat     180
tctcctacaa agaaaagttt tagagctaga aatagcaagt taaaataagg ctagtccgtt     240
atcaacttga aaaagtggca ccgagtcggt ggtgcttttt ttgttttttta tgtcttcgta     300
cgctcctaaa agtagagtta aaagtccaga aaaaaggtac gcttcaacaa ctaatgtacc     360
tagtaggcag gagtttcatt cttctactgg tacccaattc gccctatagt gagtcgtatt     420
acgcgcgctc actg                                                      434
```

<210> SEQ ID NO 16
<211> LENGTH: 868
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
cgtttgaagt acaactctag attttgtagt gccctcttgg gctagcggta aaggtgcgca      60
ttttttcaca ccctacaatg ttctgttcaa aagattttgg tcaaacgctg tagaagtgaa     120
agttggtgcg catgtttcgg cgttcgaaac ttctccgcag tgaaagataa atgatcaaaa     180
agtcaaaatt aaacaagttt tagagctaga aatagcaagt taaaataagg ctagtccgtt     240
```

-continued

```
atcaacttga aaaagtggca ccgagtcggt ggtgcttttt ttgtttttta tgtcttcggt      300
gaagaatgaa cctgcatcaa gtcaaatgga tatattttct cagtagcact ttcatgcctg      360
actacgtcaa ctattggagg cggtttatgg tacccaattc gccctatagt gagtcgtatt      420
acgcgcgctc actgcgtttg aagtacaact ctagattttg tagtgccctc ttgggctagc      480
ggtaaaggtg cgcattttt cacaccctac aatgttctgt tcaaaagatt ttggtcaaac       540
gctgtagaag tgaaagttgg tgcgcatgtt tcggcgttcg aaacttctcc gcagtgaaag      600
ataaatgatc aaaaagtcaa aattaaacaa gttttagagc tagaaatagc aagttaaaat      660
aaggctagtc cgttatcaac ttgaaaaagt ggcaccgagt cggtggtgct ttttttgttt      720
tttatgtctt cggtgaagaa tgaacctgca tcaagtcaaa tggatatatt ttctcagtag      780
cactttcatg cctgactacg tcaactattg gaggcggttt atggtaccca attcgcccta      840
tagtgagtcg tattacgcgc gctcactg      868
```

<210> SEQ ID NO 17
<211> LENGTH: 868
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
cgtttgaagt acaactctag attttgtagt gccctcttgg gctagcggta aggtgcgca       60 tttttttcaca ccctacaatg ttctgttcaa aagattttgg tcaaacgctg tagaagtgaa    120
agttggtgcg catgtttcgg cgttcgaaac ttctccgcag tgaaagataa atgatcgttt     180
gcaagaaatg ttacgcgttt tagagctaga aatagcaagt taaataagg ctagtccgtt      240 atcaacttga aaaagtggca ccgagtcggt ggtgcttttt ttgtttttta tgtcttcgaa     300
caaagctgct aacgaaatga agagcgtttg caagaaatg ttacgctaag caggcgtgaa     360
tatttcggag ctcttaattg gtacttttgg tacccaattc gccctatagt gagtcgtatt     420
acgcgcgctc actgcgtttg aagtacaact ctagattttg tagtgccctc ttgggctagc     480
ggtaaaggtg cgcattttt cacaccctac aatgttctgt tcaaaagatt ttggtcaaac      540
gctgtagaag tgaaagttgg tgcgcatgtt tcggcgttcg aaacttctcc gcagtgaaag     600
ataaatgatc gtttgcaaga atgttacgc gttttagagc tagaaatagc aagttaaaat     660
aaggctagtc cgttatcaac ttgaaaaagt ggcaccgagt cggtggtgct ttttttgttt     720
tttatgtctt cgaacaaagc tgctaacgaa atgaaagagc gtttgcaaga atgttacgc      780 taagcaggcg tgaatatttc ggagctctta attggtactt ttggtaccca attcgcccta     840
tagtgagtcg tattacgcgc gctcactg      868
```

<210> SEQ ID NO 18
<211> LENGTH: 868
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
cgtttgaagt acaactctag attttgtagt gccctcttgg gctagcggta aggtgcgca       60 tttttttcaca ccctacaatg ttctgttcaa aagattttgg tcaaacgctg tagaagtgaa    120
agttggtgcg catgtttcgg cgttcgaaac ttctccgcag tgaaagataa atgatcatga    180
```

```
catatcaata gaaagggttt tagagctaga aatagcaagt taaaataagg ctagtccgtt      240
atcaacttga aaaagtggca ccgagtcggt ggtgctttt ttgttttta tgtcttcgtt       300 agatctatcc gatgaggagt tattaaatga catatcaata gaaaggtaaa gagagctttt     360
gggctcgaaa aagacgaaaa aaataaaagg tacccaattc gccctatagt gagtcgtatt     420
acgcgcgctc actgcgtttg aagtacaact ctagattttg tagtgccctc ttgggctagc     480
ggtaaaggtg cgcattttt cacaccctac aatgttctgt tcaaaagatt ttggtcaaac      540
gctgtagaag tgaaagttgg tgcgcatgtt tcggcgttcg aaacttctcc gcagtgaaag     600
ataaatgatc atgacatatc aatagaaagg ttttagagc tagaaatagc aagttaaaat      660
aaggctagtc cgttatcaac ttgaaaaagt ggcaccgagt cggtggtgct tttttgttt     720 tttatgtctt cgttagatct atccgatgag gagttattaa atgacatatc aatagaaagg     780
taaagagagc ttttgggctc gaaaaagacg aaaaaaataa aaggtaccca attcgcccta     840
tagtgagtcg tattacgcgc gctcactg                                        868
```

```
<210> SEQ ID NO 19
<211> LENGTH: 898
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
cgtttgaagt acaactctag attttgtagt gccctcttgg gctagcggta aggtgcgca       60 ttttttcaca ccctacaatg ttctgttcaa agattttggt caaacgctg tagaagtgaa     120 agttggtgcg catgtttcgg cgttcgaaac ttctccgcag tgaaagataa atgatcccat     180
tctcctacaa agaaaagttt tagagctaga aatagcaagt taaaataagg ctagtccgtt     240
atcaacttga aaaagtggca ccgagtcggt ggtgctttt ttgttttta tgtcttcgta       300 cgctcctaaa agtagagtta aaagtccaga aaaaaggtac gctagtggag ggggcagctc     360
aacaactaat gtacctagta ggcaggagtt tcattcttct actggtaccc aattcgccct     420
atagtgagtc gtattacgcg cgctcactgc gtttgaagta caactctaga ttttgtagtg     480
ccctcttggg ctagcggtaa aggtgcgcat ttttcacac cctacaatgt tctgttcaaa      540
agattttggt caaacgctgt agaagtgaaa gttggtgcgc atgtttcggc gttcgaaact     600
tctccgcagt gaaagataaa tgatcccatt ctcctacaaa gaaaagtttt agagctagaa     660
atagcaagtt aaaataaggc tagtccgtta tcaacttgaa aaagtggcac cgagtcggtg     720 gtgcttttt tgttttttat gtcttcgtac gctcctaaaa gtagagttaa aagtccagaa     780
aaaaggtacg ctagtggagg gggcagctca acaactaatg tacctagtag gcaggagttt     840
cattcttcta ctggtaccca attcgcccta tagtgagtcg tattacgcgc gctcactg       898
```

```
<210> SEQ ID NO 20
<211> LENGTH: 898
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
cgtttgaagt acaactctag attttgtagt gccctcttgg gctagcggta aggtgcgca       60
```

```
tttttttcaca ccctacaatg ttctgttcaa aagattttgg tcaaacgctg tagaagtgaa      120
agttggtgcg catgtttcgg cgttcgaaac ttctccgcag tgaaagataa atgatcaaaa      180
agtcaaaatt aaacaagttt tagagctaga aatagcaagt taaaataagg ctagtccgtt      240
atcaacttga aaaagtggca ccgagtcggt ggtgcttttt ttgtttttta tgtcttcggt      300
gaagaatgaa cctgcatcaa gtcaaatgga tatattttct cagagtggag ggggcagcta      360
gcactttcat gcctgactac gtcaactatt ggaggcggtt tatggtaccc aattcgccct      420
atagtgagtc gtattacgcg cgctcactgc gtttgaagta caactctaga ttttgtagtg      480
ccctcttggg ctagcggtaa aggtgcgcat ttttttcacac cctacaatgt tctgttcaaa      540
agattttggt caaacgctgt agaagtgaaa gttggtgcgc atgtttcggc gttcgaaact      600
tctccgcagt gaaagataaa tgatcaaaaa gtcaaaatta aacaagtttt agagctagaa      660
atagcaagtt aaaataaggc tagtccgtta tcaacttgaa aaagtggcac cgagtcggtg      720 gtgcttttt tgtttttat gtcttcggtg aagaatgaac ctgcatcaag tcaaatggat      780
atattttctc agagtggagg gggcagctag cactttcatg cctgactacg tcaactattg      840
gaggcggttt atggtaccca attcgcccta tagtgagtcg tattacgcgc gctcactg       898

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cacccatgtc tctttgagca                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cctgttgctg ccaagctatt                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
actcttgttg catggctacg                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tggcgttcgt tgtaatggtg                                                    20
```

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gtgaaagttg gtcccaatgc                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tagcagactt cttggacgac                                                   20

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
catgagtttc tcctttggcc gtc                                               23

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
acgagccaac ttaccgtctg                                                   20

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gcaggaagtt gagttgca                                                     18

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
caggcatttc gtatgtc                                                      17
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
agttggctgc cccctccact                                                     20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggcatgctgc cccctccact                                                     20

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gctgaagaag aataggagcg ag                                                  22

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acgcactcta gtcagcaaac                                                     20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aaagccgcct gctgaagatg                                                     20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ccatttgact tgatgcaggt tc                                                  22

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cattagttgt tgaagcgtac c                                              21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggcatgaaag tgctactgag                                                20

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccatcacaga catatcacca cg                                             22

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gttgagctgc cccctccact                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tgctagctgc cccctccact                                                20

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgtctcggat c                                                         11

<210> SEQ ID NO 43

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gccgtcacat aacttaagaa                                              20

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gtttgaagag catacgctct tctcca                                       26

<210> SEQ ID NO 45
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ggatagcctg gaatacgaaa tctttgtctt cctgtaaagt taccgccttg tgtgtacgtg   60
tatgattttt taaatatata                                              80

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aagggagcac aaatggttaa                                              20

<210> SEQ ID NO 47
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tcgcgatgtg cttttggata gcctggaata cgaaatcttt cggcttcgtc accattaccg   60
ccttgtgtgt acgtgtatga                                              80

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
acatcgagac g                                                       11
```

```
<210> SEQ ID NO 49
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gttttagagc tagaaatagc aagttaaaat aaggctagtc cgttatcaac ttgaaaaagt        60
ggcaccgagt cggtggtgct tttttgttt tttatgtct                                99
```

LIBRARY-SCALE ENGINEERING OF METABOLIC PATHWAYS

RELATED APPLICATIONS

This application is a National Stage Application under 35 U.S.C. 371 of co-pending PCT application PCT/US17/36985 designating the United States and filed Jun. 12, 2017; which claims the benefit of U.S. provisional application No. 62/348,438 filed on Jun. 10, 2016 each of which are hereby incorporated by reference in their entireties.

STATEMENT OF GOVERNMENT INTERESTS

This invention was made with government support under HG008525 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 7, 2018, is named "Sequence Listing" and is 45,688 bytes in size.

TECHNICAL FIELD OF THE INVENTION

This invention is related to the area of in vitro genetic manipulation. In particular, it relates to use of synthetic oligonucleotides in genetic manipulation.

BACKGROUND OF THE INVENTION

Bacterial and archaebacterial innate immunity systems have been widely found among many species. Typically, these systems involve an endonuclease that is guided by a nucleic acid, either an RNA or a DNA. The guide nucleic acid renders the endonuclease exquisitely specific. After a specific break in double stranded DNA of a cell has occurred, repair of the break can occur by host recombination systems. If a homologous or partially homologous oligonucleotide is supplied, integration can occur at the locus of the break.

The CRISPR type II system, one of these innate immunity systems, has been used to edit the genomes of a broad spectrum of species (see, e.g., Friedland et al., 2013; Mali et al., 2013; Hwang et al., 2013; Jiang et al., 2013; Jinek et al., 2013; Cong et al., 2013; Yin et al., 2014). CRISPR is particularly customizable because the active form consists of an invariant Cas9 protein and an easily programmable single guide RNA (sgRNA). Jinek et al., 2012. Of the various CRISPR orthologs, the *Streptococcus pyogenes* (Sp) CRISPR is the most well-characterized and widely used. The Cas9-gRNA complex first probes DNA for the protospacer-adjacent motif (PAM) sequence (-NGG for Sp Cas9), after which Watson-Crick base-pairing between the sgRNA and target DNA proceeds in a ratchet mechanism to form an R-loop. Following formation of a ternary complex of Cas9, sgRNA, and target DNA, the Cas9 protein generates two nicks in the target DNA, creating a blunt double-strand break (DSB) that is repaired by the non-homologous end joining (NHEJ) pathway or template-directed homologous recombination (HR). CRISPR methods are disclosed, for example, in U.S. Pat. Nos. 9,023,649 and 8,697,359, the disclosures of which are expressly incorporated here.

Metabolic engineering allows enhanced production of chemicals, fuels, and medicine. To achieve high levels of metabolite production, metabolic pathways are typically transplanted into various host organisms from other organisms. Biosynthetic pathway construction and optimization requires large-scale manipulation of native and heterologous genes For several decades, the standard method of introducing or removing genes from organisms relied on gene targeting by PCR-generated marker cassettes. These techniques were often limited by the limited number of unique selection markers that work in an organism of interest. Limited selection markers limits the number of genes that can be removed and heterologous genes that can be inserted easily. Additionally, such techniques require successive rounds of screening to achieve desired organisms with multiple genes introduced or modified. Such techniques are time-consuming and highly inefficient.

There is a continuing need in the art to develop faster and more efficient techniques for metabolic engineering of production cells as well as cellular engineering for other purposes.

SUMMARY OF THE INVENTION

According to one embodiment of the invention a method is provided for generating a library of mutant yeast cells. The mutant yeast cells carry a mutation in a nucleic acid segment. Mutant cells within the library carry different mutations within the nucleic acid segment. A library of oligonucleotides is synthesized on an array. Each oligonucleotide comprises: (a) a segment encoding a guide nucleic acid which is complementary to a target site in a nucleic acid in a yeast cell, and (b) a donor DNA comprising the nucleic acid segment which is flanked by two sequences which are complementary to two regions of the nucleic acid. The two regions are on opposite sides of the target site. The nucleic acid segment comprises a mutation. The oligonucleotides of the library are incorporated into a plasmid vector to form a library of plasmids. The donor DNA in the library of plasmids comprises at least 24 distinct mutations in the nucleic acid segment and each mutation is on a separate oligonucleotide molecule. A yeast cell which expresses a nucleic acid-guided endonuclease is transformed with the library of plasmids. The guide nucleic acid is expressed in the yeast cell. The nucleic acid-guided endonuclease breaks the nucleic acid at the target site. The donor DNA recombines with the nucleic acid at the two regions via the two sequences which are complementary, rejoining two portions of the nucleic acid that had been separated by breakage of the nucleic acid by the nucleic acid-guided endonuclease. Transformed yeast cells are then recovered.

Another aspect of the invention is a method of generating a library of carrier plasmids in which the carrier plasmids carry a mutation in a nucleic acid segment of a target cell, and the carrier plasmids within the library carry different mutations in the nucleic acid segment. A library of oligonucleotides is synthesized on an array. Each oligonucleotide comprises: (a) a segment encoding a guide nucleic acid which is complementary to a target site in a nucleic acid in the target cell, and (b) a donor DNA comprising the nucleic acid segment which is flanked by two sequences which are complementary to two regions of the nucleic acid of the target cell. The two regions are on opposite sides of the target site, and the nucleic acid segment comprises a mutation. The library of oligonucleotides is incorporated into a backbone plasmid. The oligonucleotides and the backbone plasmid form a circularized plasmid in which the segment encoding the guide nucleic acid is operably linked downstream from a promoter. The donor DNA in the library of oligonucleotides comprises at least 24 distinct mutations each on a separate molecule of donor DNA.

In still another aspect of the invention a library of mutant yeast cells is provided. The mutant yeast cells carry a mutation in a nucleic acid segment. The mutant cells within the library carry at least 1000 distinct mutations in the nucleic acid segment in at least 1000 distinct yeast cells. The mutant yeast cells further comprise a gene encoding a nucleic acid-guided endonuclease and a plasmid. The plasmid comprises: (a) a segment encoding a guide nucleic acid which is complementary to a target site in a nucleic acid in the yeast cell, and (b) a donor DNA comprising the nucleic acid segment which is flanked by two sequences which are complementary to two regions of the nucleic acid. The two regions are on opposite sides of the target site. The segment comprises a mutation.

Yet another aspect of the invention is a library of carrier plasmids in which the carrier plasmids carry a mutation in a segment of a nucleic acid of a target cell. The carrier plasmids within the library carry different mutations in the segment of the nucleic acid. The nucleic acid segment is flanked by two sequences which are complementary to two regions of the nucleic acid. The two regions are on opposite sides of a target site. The carrier plasmids further comprise a segment encoding a guide nucleic acid which is complementary to the target site. The segment encoding the guide nucleic acid is operably linked downstream from a promoter. The library comprises at least 1000 distinct mutations each in a distinct plasmid.

One aspect of the invention is a library of oligonucleotides. The oligonucleotides comprise (a) a segment encoding a guide nucleic acid which is complementary to a target site in a nucleic acid of a target cell; and (b) a donor DNA comprising a nucleic acid segment which is flanked by two sequences which are complementary to two regions of the nucleic acid of the target cell. The two regions are on opposite sides of the target site. The nucleic acid segment comprises a mutation. The donor DNA in the library of oligonucleotides comprises at least 1000 distinct mutations each on a separate molecule of donor DNA.

These and other embodiments which will be apparent to those of skill in the art upon reading the specification provide the art with tools and methods for generating systematic diversity in a target nucleic acid.

BRIEF DESCRIPTION OF THE DRAWINGS

FIG. 1 is a schematic drawing which depicts the components of guide plus donor, 170 nt, oligonucleotide libraries. Two sample oligonucleotides are displayed. Restriction endonuclease sites (exemplified here as BsmB1 and SapI) are to aid in assembly of the ultimate transfecting/transforming molecules.

FIG. 2 is a schematic drawing which depicts the assembly of amplified oligonucleotides into a cloning vector. The vector has a selectable selectable marker (Ura3) and a site for insertion of a fragment with ends complementary to a cleaved BsmBI site.

FIG. 6 is a schematic drawing that depicts the amplification of a fragment of the selectable marker that overlaps with the gap in the plasmid molecule.

FIG. 7 is a schematic drawing that depicts the co-transformation of a yeast cell with the gapped plasmid (see FIG. 5) and the fragment that overlaps with the gap in the gapped plasmid (see FIG. 6).

DETAILED DESCRIPTION OF THE INVENTION

Figure 3:
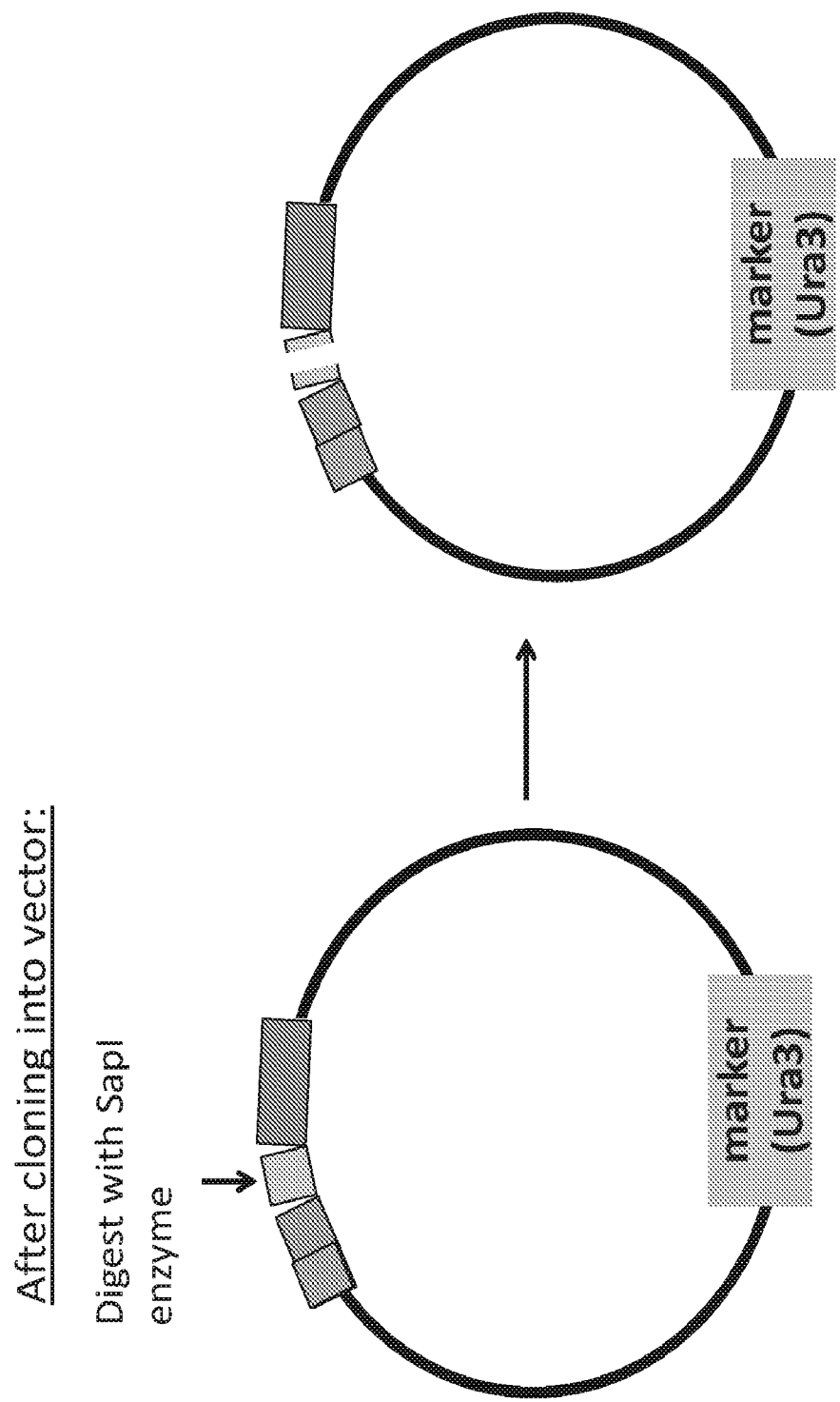
FIG. 3 is a schematic drawing which depicts the opening of the vector for a second insertion using a different restriction endonuclease which cuts an internal site in the guide plus donor oligonucleotide insert.
Figure 4:
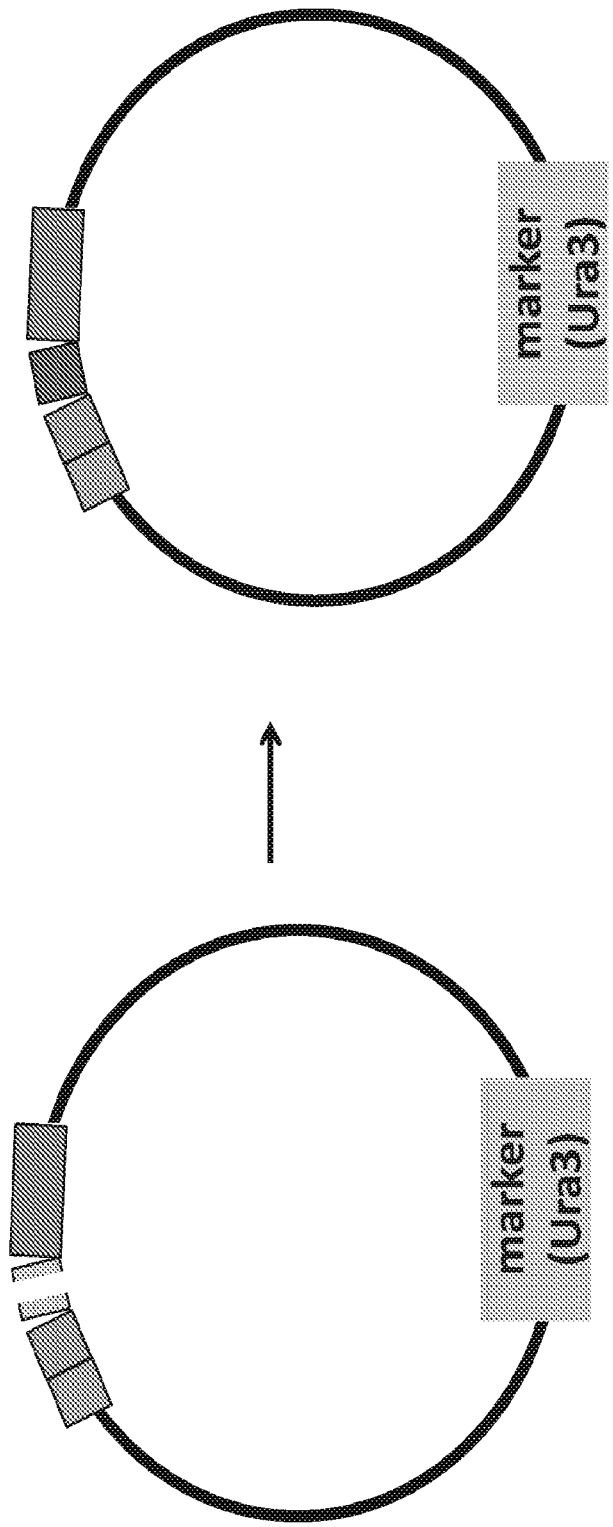
FIG. 4 is a schematic drawing that depicts the insertion of the second segment into the linearized plasmid. The second insert contains the guide RNA tail (also termed the sgRNA tail) and a terminator from the yeast SUP4 gene. The guide RNA tail is essentially invariant, while the guide plus donor sequences are variable.
Figure 5:
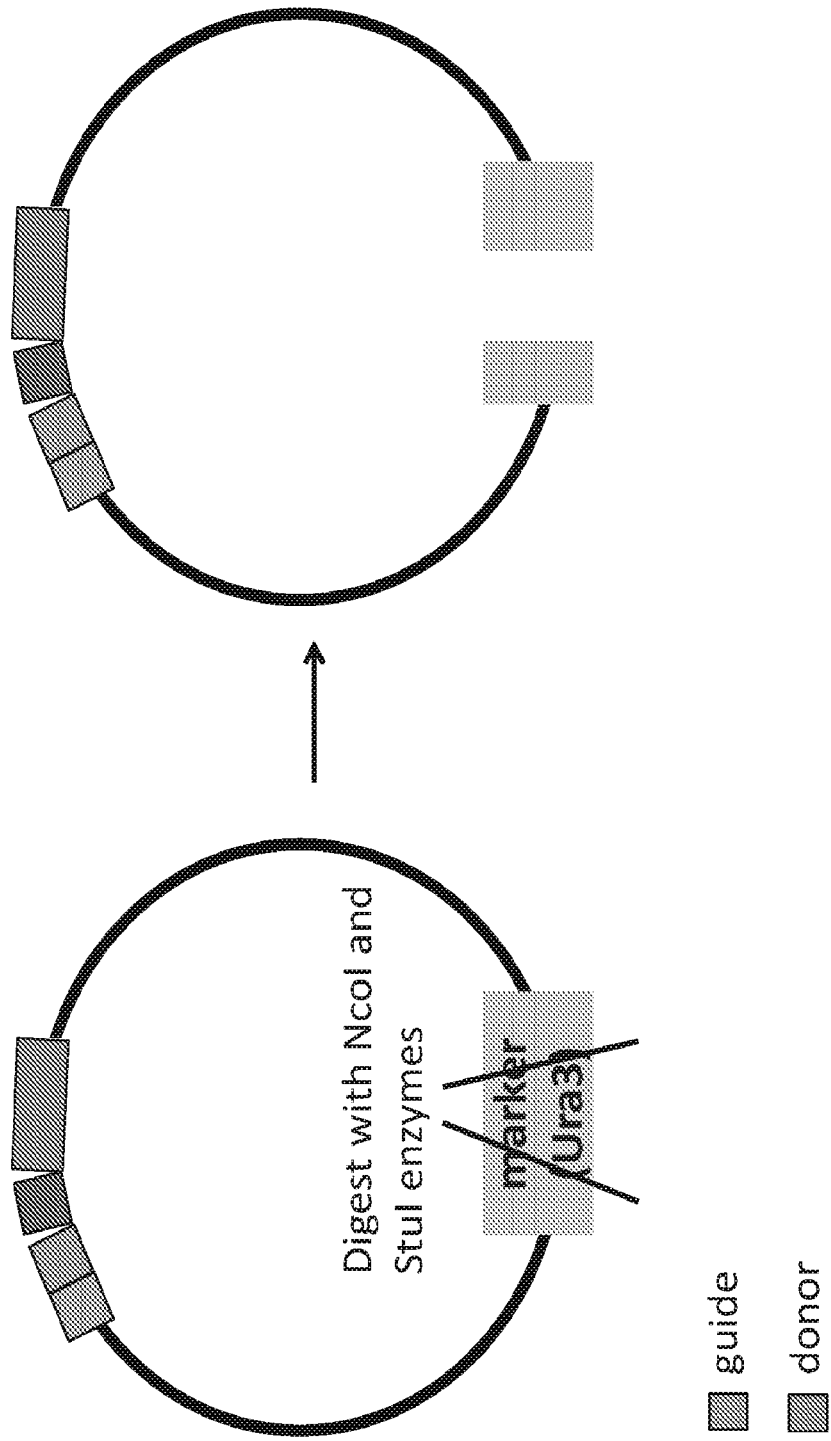
FIG. 5 is a schematic drawing that depicts the linearization and gapping of the plasmid molecule by removal of a portion of the selectable marker.

The inventors have developed a highly efficient method for generating complex libraries of plasmids and cells with comprehensive diversity in regions of interest. The method permits making of a variety of types mutations in any particular region and permits the layering of mutations in the same cells by repeated rounds of engineering.

Synthesis of oligonucleotides on a solid array can be accomplished according to techniques which are known in the art. Exemplary arrays and techniques include those available from or used by Custom Array DNA (Bothell, WA), MYcroarray, and LC Sciences. Oligonucleotides that are synthesized will contain sequences encoding guide RNA and donor sequence to be introduced into a genome, chromosome, etc. All of the guide RNA may not be synthesized as part of the oligonucleotide. The guide RNA may be considered as comprising a guide head and a guide tail. The guide head is about 15-22 bases in length, about 17-21 bases in length, or about 18-20 bases in length. The guide head is related in sequence to the donor DNA. The guide tail is longer and will generally be invariant in a population of plasmid constructs. The guide tail may be between about 90 and 110 bases, between about 95 and 105 bases, or between about 98 and 100 bases. The guide tail, due to its general invariance, need not be synthesized on the solid array, but can be separately synthesized by any means, including by PCR, solid phase synthesis, or recombinant synthesis. The guide tail can be joined to the oligonucleotide (containing the guide head) separately or at the same time as the oligonucleotide is joined to the plasmid.

Guide nucleic acids may be RNA or DNA molecules. They are selected and coordinated with the nucleic acid-guided endonuclease, i.e., the properties of the guide are dictated by the endonuclease. Many such endonucleases are known. Some estimate that about one half of all bacterial species have a nucleic acid-guided endonuclease as part of an innate immunity system. An exemplary and well-studied endonuclease is Cas9. Other examples include PfAgo, NgAgo, as well as orthologs of Cas9 from *Steptococcus thermophilus, Lactobacillus gasseri, Staphylococcus aureus, Francisella novicida, Wolinella succinogenes, Sutterella wadsworthensis, Gamma proteobacterium, Neisseria meningitidis, Camplyobacteri jejuni, Fibrobacter succinogenes, Rhodobacter speaeroides, Thermus thermophilus, Pyrococcus pyogenes*, and *Rhodospirillum rubrum.*

Guide nucleic acids are selected for complementarity to a target site of interest. Desirably the complementarity will be complete within the guide head, but for the desired mutation. Decreased complementarity may lead to loss of specificity and/or efficiency. The guide will be expressed from the plasmid in the case of a guide RNA. To achieve such expression, a suitable promoter will be placed upstream of the guide RNA-coding segment on the carrier plasmid. The transcription promoter may be synthesized as part of the oligonucleotide or may be a part of the plasmid vector. A transcription terminator may optionally be placed downstream from the guide RNA-coding segment. A terminator may prevent read-through transcription of donor nucleic acid. Any terminator functional in yeast cells, or other desired host cells, known in the art may be used.

Like the guide RNA, the donor DNA will desirably be highly complementary to the target site. Desirably, the only lack of complementarity will be the mutation that is introduced by oligonucleotide synthesis. This may be a single nucleotide or more, in the case of insertions and deletions. The insertions and deletions may be small, e.g., 1, 2, 3, or 4 basepairs, or it may be larger, such as about 5, 10, 15, 20, 25, 30, 35, 40, 50, 60, 70, 75, 80, 100 basepairs, or more. In some embodiments, at least 18, at least 25, at least 30, at least 35, at least 40, at least 45, at least 50, at least 75, or at least 100 bp of complementarity on either side of the mutation (i.e., flanking the mutation) is desirable to achieve efficient recombination of the donor DNA into the target nucleic acid. Typically the length of the donor DNA will be about 36-200 bp, about 50-150, about 60-100 bp. Alternatively the donor may be within any range with a low end of 35, 40, 45, or 50 and a high end of 100, 150, 200, or 250 bp. If a large insertion is desired, longer overall donor lengths may be used.

Plasmids which can be used in the methods described include any that have an origin of replication that is functional in the target cells. These plasmids will typically be linearizable. Often such linearization will be accomplished with a restriction endonuclease that cleaves the plasmid one or a few times only. Other methods, enzymatic or mechanical can be used for linearization. Often the plasmid will have one or more markers that are selectable or easily screenable in an intermediate host cells and/or in the target cells. For example, an antibiotic resistance gene can be used for selecting in a host cell, such as *E. coli*, and a prototrophic marker to complement an auxotrophy can be used for selecting in yeast cells. Transcription regulatory elements such as promoters and terminators may also be in the plasmid for controlling transcription of elements of the oligonucleotide.

The oligonucleotides of the library that are synthesized on an array can be incorporated in a plasmid vector or backbone. Any means for assembling the library of plasmids from a library of oligonucleotides and plasmid backbone can be used as is convenient. The assembly can be in vitro or in vivo in cells. One such means is Gibson Assembly which permits assembly of multiple DNA fragments, regardless of fragment length or end compatibility. Gibson Assembly employs three different enzymes: an exonuclease creates single-stranded 3' overhangs; a DNA polymerase fills in gaps after fragments anneal to each other via the overhangs; and a DNA ligase seals nicks in the assembled DNA. Other methods for joining DNA fragments can be used. When an oligonucleotide is incorporated into a plasmid a carrier plasmid is formed. An alternative embodiment transforms recipient cells with the plasmid vector or backbone and the oligonucleotide and recombination occurs in recipient cells using cellular enzymatic machinery. After construction of the library of carrier plasmids, by incorporation of the oligonucleotide library into the backbone plasmid, the library can be amplified and or maintained by growth in appropriate host cells.

Promoters for expressing the guide nucleic acid may be synthesized as part of the oligonucleotides or can be part of the backbone plasmid. This is a matter of design choice. The promoter may be one that expresses constitutively in the host cell or one that is inducible or one that is repressible. Control of the promoter is a matter of design choice.

Barcodes may be used to identify guide and donor DNA oligonucleotides. The barcode may be used to identify individual molecules of a population of a particular guide and donor DNA. Alternatively, a barcode may be used to identify all members of such a population of a particular guide and donor DNA. Another option would be to use a barcode to identify sets of guide and DNA oligonucleotides that share some property in common. Barcodes may be synthesized as part of the oligonucleotide synthesis. Barcodes may be added to or made as part of plasmid vector backbone. Barcodes may be synthesized as part of a selectable marker fragment. The placement of the barcode in a construct is a matter of design choice and the purpose to which the barcodes will be used. The barcode may be in any location where it does not compromise function of the guide and donor RNA. Alternatively, the guide and donor sequences in the plasmid may be used as an endogenous barcode. They may be used to distinguish one mutant from another in a whole population of transformants.

Libraries of mutant oligonucleotides, libraries of carrier plasmids, and libraries of mutant yeast cells may contain a collection of different mutations. The number of different mutations represented in a library may range, for example, from 20, 25, 30, 40, 50, 100, 250, 500, 750, 1,000, 2,000, 5,000, 10,000, 100,000, or 1,000,000 to any of 100, 1,000, 10,000, 100,000, 1,000,000, 10,000,000 or 100,000,000. Ranges with any of these lower and upper limits are contemplated. Different mutations within the library may optionally code for the same amino acids, for example, when looking for optimization of translation. Alternatively, no synonymous mutations may be used within a single library. In some libraries, it may be desirable to make a mutation in every nucleotide or every codon. In other libraries it may be desirable to make all possible mutations in a codon by one or more nucleotide changes. In still other libraries it may be desirable to make mutations in a codon that lead to all possible amino acid changes.

Any type of mutation that is desirable to build into an oligonucleotide may be used. Mutations may be point mutations, deletion mutations, or insertion mutations, for example. Inserted nucleic acid within an insertion mutation may be heterologous or native to the yeast host cell.

The nucleic acid of the donor DNA may be any in which mutations are desired. The donor DNA may be a promoter or other regulatory sequence. The donor DNA may be a protein-coding or RNA-coding sequence. The donor DNA may be of unknown function.

Host cells which can be used are any that can be transformed with nucleic acids or otherwise made to efficiently take up nucleic acids. The host cells may be those that naturally make useful products or those that are engineered to make useful products. Among the yeast, *Saccharomyces cerevisiae* can be used as described below. Other yeast species, such as *Pichia pastoris* or *Kluyveromyces lactis*, can also be used, both of which are commonly used as a hosts for the production of biopharmaceuticals and industrial enzymes. Other cell types that are amenable to transformation can be used as host cells as well. These include without limitation bacteria, such as *Escherichia coli*, and human cells, including human cell lines. These may be particularly useful for engineering of therapeutic protein products.

Any means of transformation of cells can be used. However, high efficiency of transformation is desirable. One feature that contributes to high efficiency is the linkage of nucleic acid encoding guide nucleic acid to nucleic acid encoding donor nucleic acid. Such linkage insures that any transformed cell has both components necessary for making a mutation in the host cell. Another feature that may contribute to high efficiency of transformation of yeast cells is the use of DMSO, for example, DMSO at a final concentration of 10%, prior to a step of heat shock. Other amounts of DMSO may be used for example 5, 6, 7, 8, 9, 11, 12, 13, 14, 15, or 16 percent. In general, any technique known in the art for yeast transformation can be used, including but not limited to use of lithium, electroporation, biolistic and glass bead methods. Transformation efficiencies, depending on the host cell, and the particular elements used in the transforming nucleic acids, may vary, for example, from at least 20, at least 25, at least 30, at least 35, at least 40, at least 45, at least 50, at least 60, at least 70, at least 80, at least 90, or at least 95% up to 100%.

Yeast cells used as recipients of the carrier plasmid library may express a nucleic acid-guided endonuclease. Typically this will be a heterologous enzyme that the yeast has been previously engineered to express. Any of the nucleic acid-guided endonucleases may be used. Any technique known in the art for introducing and expressing a nucleic acid encoding the endonuclease may be used. Alternately, a nucleic acid encoding the endonuclease may be introduced with the plasmid into the yeast. Another option is to introduce the endonuclease after addition of the plasmid library. Selection among such options is within the skill of the art.

Transformed yeast cells can be recovered (i.e., isolated and purified) by selection for a marker on the plasmid, such as a marker that complements an auxotrophic mutation. Suitable auxotrophies and their complementing markers are well known in the art, and include without limitation LEU$^-$, HIS$^-$, and URA$^-$. Other markers such as antibiotic resistance markers can also be used. Recovered cells can be colony purified and analyzed. Analysis of the transformed yeast cells may include sequencing of the plasmids that are contained in them. The sequencing may be targeted to the segment encoding the guide RNA and the donor DNA. If a barcode is present, the sequencing may be targeted to the barcode as a surrogate for the guide RNA and the donor DNA. Any method for determining the sequence may be used. For library analysis, a massively parallel sequencing technique can be used. Typically such techniques involve amplification before sequencing, often onto a solid support, such as a bead, slide, or array. Such sequencing techniques typically involve short overlapping reads, and high coverage.

A nucleic acid target site in a yeast cell, which is complementary to the guide nucleic acid, may be in any compartment of the yeast cell. It may be, for example, genomic, it may be mitochondrial, or it may be extrachromosomal. These can be selected for a particular overall purpose.

In one embodiment the method may employ guide RNA (gRNA)-targeted Cas9 to make site-specific cuts. The gRNA and donor duplexes will typically be introduced to a target cell encoded on the same vector, such as a plasmid. This ensures that a host cell will have both components, rather than requiring a host cell to be transformed by two different vectors. Thus the efficiency of successful transformations is markedly increased. This is a great improvement in efficiency over approaches in which gRNA and donor are encoded on separate molecules. The Cas9 protein may be expressed by the recipient host cells. This can be accomplished by a prior introduction by a standard means.

In one aspect of the invention a multiplex transformation of cells achieves thousands of distinct genetic modifications in a targeted fashion and at high efficiency. Oligonucleotide chip array technology is used to synthesize hundreds of thousands of distinct oligonucleotides, each encoding a gRNA with a corresponding donor sequence.

In another aspect of the invention, gRNA is associated with a corresponding donor sequence in one plasmid. This permits simultaneous delivery of every gRNA with its donor sequence into the cell. Expressing gRNA from the same oligonucleotide containing the donor sequence allows simultaneous transformation of both substrates into a population of cells.

In addition, improved transformation conditions can be combined with the multiplex transformation and with the single plasmid delivery of guide nucleic acid and donor nucleic acid to achieve extremely high efficiency levels.

The oligonucleotide synthesis of the combined guide and donor nucleic acids can be used to generate any desired type of mutation. Insertion (heterologous or endogenous), deletion, nonsense, silent, conservative, duplication, and higher order duplications can all be achieved via this method. As described below, we have tested our method for making such high value genetic modifications as deleting targeted regions or inserting small sequences into the genome.

The combined improvements lead to greatly reduced costs for the engineering of libraries of mutants of various types. The reduced costs make massive scale engineering possible for what previously has been prohibitively costly in time and resources.

In addition to guide and donor regions, plasmids may in some embodiments include barcode DNA sequences that can be used to identify independent transformants of the same guide+donor construct. Each independent transformation of a guide+donor construct identified by a unique barcode sequence is called a lineage. The number of lineages per guide+donor construct may be small (2), or large ($10^1$, $10^2$, $10^3$, etc). A single barcode may optionally be used to identify all guide+donor molecules having the same sequence. A single molecule can optionally be used to identify chosen subsets of guide+donor molecules.

Tracking the frequency of lineages within the population (i.e., the frequency of the barcode for a particular guide+donor construct), enables the effects of a particular mutation introduced by the combined guide+donor sequence to be more accurately determined. For example, the frequency of a particular lineage can be determined by DNA sequencing; one possible method is to use massively parallel sequencing. Other methods may be employed. By tracking lineage frequency within the plasmid library and within the transformed yeast population, one can determine whether the guide RNA has successfully mediated cutting of the genome and whether the donor DNA has successfully repaired the cut and introduced the target mutation into the genome.

In some embodiments, the degeneracy of the barcode sequences may be much larger than the number of distinct guide+donor constructs. For example, a barcode with 20 degenerate N nucleotides would have $4^{20} \sim = 10^{12}$ unique sequences. In this way, most barcode sequences will be linked to a unique guide+donor construct. After having determined the nucleotide sequences of the barcode, guide, and donor within the plasmid library, the frequencies of each lineage may then be measured simply by sequencing the DNA barcode region of the plasmid library, without the need to sequence the guide and donor regions.

A barcode may be inserted in any location of the plasmid. In some instances, the barcode may be incorporated into the plasmid within the small guide RNA (sgRNA) spacer sequence at the end of the sgRNA tail insert, so that it will be nearest to the donor region of the plasmid. The barcode may be immediately adjacent or not to the guide or the donor sequences. It may precede or follow the guide or donor. In another instance, the barcode may be incorporated within a PCR-amplified selectable marker, such as a URA3 fragment. In another instance, the barcode may be incorporated at either end of the donor DNA sequence as synthesized in the oligonucleotide pool. In other instances the barcode may be split into two or more locations anywhere on the plasmid, for example on both ends of the donor sequence. The barcode may appear in more than one location on the plasmid, or on the plasmid and on the selectable marker.

The methods that we describe can be used to engineer metabolic systems to push metabolic flux towards products of interest. For example, promoter engineering and combinatorial modifications of native and heterologous genes in metabolic pathways are crucial for increasing metabolic output. Moreover, our method can be applied to populations of cells that can be transformed repeatedly to rapidly obtain cells with, for example, optimized pathways giving maximum output, or new products due to combination of different metabolic pathways.

The methods that we describe can be used to rapidly generate protein variants for functional characterization of any protein-of-interest. The methods can be used for domain deletion, amino acid replacement, and protein tagging, all of which are common approaches for elucidating protein function.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Results

To test the genetic modification efficiency of our single oligo design plus optimized delivery platform, we constructed gRNA+donor oligos targeting two genes: an endogenous gene (SGS1) and exogenous gene (CAS9).

Table 1 below shows types of modifications and percentages of successful modifications for each gene.

| Gene targets | Types of modifications | Frequency of success | Frequency of success (%) |
|---|---|---|---|
| SGS1 | Point mutation | 23/24 | 96% |
| | Deletion (60 bp) | 24/24 | 100% |
| | Insertion (15 bp) | 7/7 | 100% |
| CAS9 | Point mutation | 20/24 | 83% |
| | Deletion (60 bp) | 22/24 | 92% |
| | Insertion (15 bp) | 21/24 | 88% |

The methods that we describe can be scaled up to library size to generate thousands of protein variants that include all the above types of modifications at once.

Example 2—Materials and Methods

Strain Construction

All yeast strains used in this study were derived from BY4741 (MATa his3Δ1 leu2Δ0 met15Δ0 ura3Δ0). YAC2563 contains a NOP1-hCas9 allele and a NatMX selectable marker integrated at the HO locus by transformation with PmeI-digested AC6218. The MUS81 or EXO1 gene was deleted by one-step gene replacement using PCR-generated deletion cassettes amplified from pUG6 plasmid containing KANMX selection marker.

Media and Growth Conditions

All growth of yeast was at 30° C. Cells were grown nonselectively in YPD (1% yeast extract sold under the trade name BACTO™ yeast extract, 2% peptone sold under the trade name BACTO™ peptone, 2% dextrose). Ura+ colonies were selected on minimal media supplemented with histidine, leucine, methionine, and adenine hemisulfate.

Plasmid Construction

AC6218 (pNEB193-HO-nop1:Cas9-NATMX) was constructed using DNA assembly kit sold under the trade name GIBSON ASSEMBLY® into the base vector pNEB193. Full plasmid sequence provided within Table 2.

The gRNA+donor expression cassettes used in this study contain SNR52 promoter, gRNA, SUP4 terminator and donor sequence that shares total homology of 90 bp with the targeted chromosomal region and were synthesized as gblocks by Integrated DNA Technologies (IDT). Each gene fragment was Gibson assembled into PCR-purified NheI-KpnI (NEB)-digested p426 library base vector (sequence on Table 2) using NEB Gibson Assembly kit to generate p426-gRNA+donor expression plasmids. For a list of gblock sequences, see Table 2.

Individual Transformation of gRNA+Donor Plasmids into Cas9-Containing Cells

Circular p426 plasmid containing gRNA+donor was first linearized by NcoI and StuI (supplied by NEB) followed by gel purification to remove part of the URA3 marker sequence (plasmid sequence provided on Table 2). In parallel, PCR was performed using the intact gRNA+donor plasmid as a template to generate a URA3 fragment that can serve as a repair template for the digested vector and shares ~150 bp homology on each side with the linearized NcoI-StuI-fragment. For individual transformation, 400 ng of each fragment was co-transformed into exponentially growing cells by lithium acetate transformation (Gietz and Schiestl, 2007). gRNA+donor targeting vectors were directed against either ADE2, SGS1, or SRS2. Transformants were plated on minimal media lacking uracil and grown for 3-4 days. For DNA sequence analysis, individual Ura+transformants were PCR amplified and Sanger sequenced by sequencing technology sold under the trade name GENEWIZ™ sequencing (South Plainfield, NJ). All primers are listed on Table 3.

In Silico Design of gRNA+Donor Libraries

The sequences used to build the SGS1 and the small open reading frame (smORF) targeting libraries were downloaded from *Saccharomyces cerevisiae* Genome Database (SGD, available at a website with the domain name of yeastgenome and the top level domain of org.). The gRNAs and donor sequences for all the libraries were generated using pipelines written in programming language sold under the trade name PYTHON™ version 2.7.11 with the following design parameters. The deletion library for SGS1 contains series of staggered 60-bp-sized deletions with 20 bp (5 amino acid) overlaps. The smORF deletion library is designed to eliminate the first 60 bp of each open reading frame (ORF). The donor sequence for each deletion includes 45 bp upstream and downstream of the deletion. The point mutation library for SGS1 targets conserved residues and contains donor sequences recoding the conserved residues to alanines flanked by 45 bp homology arms.

Oligonucleotide Library Synthesis and Plasmid Library Preparation

Oligonucleotide libraries were synthesized using Custom Array DNA (Bothell, WA). Oligo libraries were amplified using Kapa qPCR kit (Wilmington, MA) and were purified using Zymo Research DNA purification columns (Irvine, CA). Golden gate assembly was used to insert the oligonucleotide libraries into the cloning vector (Library Base vector-see Table 2). Once the oligonucleotide libraries were inserted into the base vector another round of golden gate assembly was performed to insert the sgRNA tail between the spacer (N20; "guide head") sequence and the donor cassette, generating the final vector containing the SNR52 promoter-gRNA targeting sequence, gRNA tail and 90 bp donor molecule.

Library-Scale Yeast Transformation of gRNA+Donor Expression Plasmids into Cas9-Expressing Cells The plasmid library for yeast transformation was prepared as described above to generate NcoI-StuI-digested fragments with a pool of gRNAs+donors and PCR amplified URA3 fragments. For library scale transformation using lithium acetate method, the following modifications were made. 1200 ng of each fragment were co-transformed into cells in log phase, adding DMSO (to 10% final concentration) prior to 42° C. heat shock followed by plating on minimal media lacking uracil. This step of optimization yielded ~20,000 Ura+ transformants/μg. Each Ura+transformant represents successful alteration of a targeted endogenous locus. All transformants were pooled and gRNA+donor sequences on plasmids were amplified and analyzed by Illumina MiSeq.

DNA Damage Sensitivity Test

For functional characterization of essential domains of Sgs1 and essential smORFs in response to DNA damage agents, transformed yeast libraries were subjected to methyl methanesulfonate (MMS, Sigma 129986) hydroxyurea (HU, Sigma H8627) and 4-nitoquinoline N-oxide (4NQO, Sigma N8141) sensitivity testing. Upon yeast library transformation, cells were plated on 0.01% MMS, 50 mg/ml HU, or 25 mg/ml 4NQO and grown for 2 days. The gRNA+donor plasmids of survivors were pooled together, PCR amplified and sequenced by Illumina MiSeq.

Epistasis Analysis Between SGS1 Libraries and MUS81- and EXO1-Pathways

SGS1 deletion or point mutation libraries were transformed into mus81- or exo1-deleted strain backgrounds to identify Sgs1 variants displaying functional overlap with these pathways. Transformed yeasts were plated onto minimal media lacking uracil and grown for 3-4 days. The gRNA+donor plasmids of survivors were pooled together, PCR amplified and sequenced by Illumina MiSeq.

Sequences used in the examples are shown in the sequence listing, which is incorporated as part of the disclosure.

TABLE 2

| Strain Number | Name | SEQ ID NO: |
|---|---|---|
| AC6218 | pNEB193-HO-nop1: Cas9-NATMX | 1 |
| | p426 library base vector | 2 |
| AC5702 | ade2Δ5 gblock | 3 |
| AC5701 | ade2Δ11 gblock | 4 |

TABLE 2-continued

| Strain Number | Name | SEQ ID NO: |
|---|---|---|
| AC5700 | ade2Δ31 gblock | 5 |
| AC5933 | ade2Δ61 gblock | 6 |
| AC5934 | ade2Δ121 gblock | 7 |
| AC5935 | ade2Δ241 gblock | 8 |
| XG23 | sgs1Δ2071-2130 gblock | 9 |
| XG25 | sgs1Δ3841-3900 gblock | 10 |
| XG26 | sgs1-K706A gblock | 11 |
| XG28 | sgs1-1293M > STOP gblock | 12 |
| XG37 | sgs1-ins-2071-2130 gblock | 13 |
| XG38 | sgs1-ins-3841-3900 gblock | 14 |
| XG30 | srs2Δ2656-2715 gblock | 15 |
| XG41 | srs2Δ3466-3526 gblock | 16 |
| XG33 | srs2--259G > STOP gblock | 17 |
| XG34 | srs2-3157R > STOP gblock | 18 |
| XG35 | srs2-ins-2656-2715 gblock | 19 |
| XG36 | srs2-ins-3466-3526 gblock | 20 |

TABLE 3

| Primer Number | Name | SEQ ID NO: |
|---|---|---|
| PAC7067 | 5' ura3 downstream of stuI cut | 21 |
| PAC7068 | 3' ura3 upstream of NcoI | 22 |
| PXG1 | ade2 − 194F | 23 |
| PXG134 | ade2 + 938R | 24 |
| PXG34 | sgs1 + 3513F | 25 |
| PXG35 | sgs1 + 4271R | 26 |
| PXG36 | sgs1 + 1583F | 27 |
| PXG37 | sgs1 + 2392R | 28 |
| PXG38 | sgs1_deletion 2071-2130 | 29 |
| PXG43 | sgs1_deletion 3841-3900 | 30 |
| PXG57 | sgs1_insertion 2071-2130 reverse | 31 |
| PXG59 | sgs1_insertion 3841-3900 reverse | 32 |
| PXG44 | srs2 − 233F | 33 |
| PXG45 | srs2 + 682R | 34 |
| PXG46 | srs2 + 2339F | 35 |
| PXG48 | srs2 + 3429R | 36 |
| PXG50 | srs2_deleting 2656-2715 reverse | 37 |
| PXG51 | srs2_deleting 3466-3526 reverse | 38 |
| PXG53 | srs2 + 2797F | 39 |
| PXG55 | srs2_insertion_2656-2715 reverse | 40 |
| PXG56 | srs2_insertion_3466-3526 reverse | 41 |

Example 3—Recovery of Engineered Mutant Strains

Figure 8A:
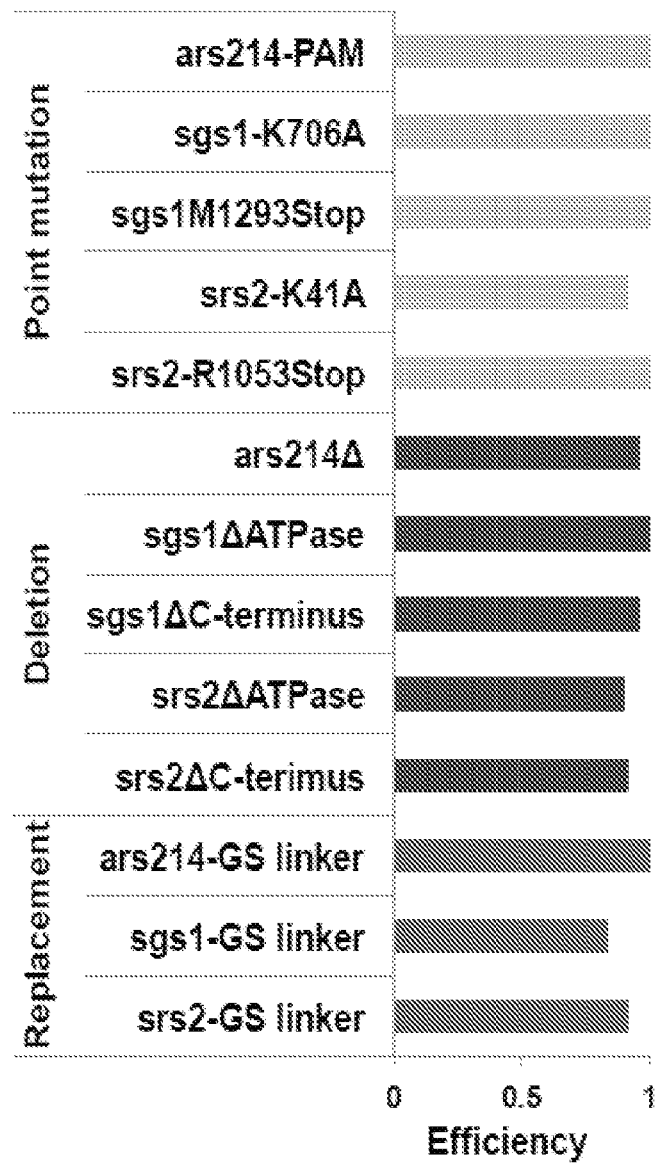
FIG. 8A is a bar graph of data evidencing recovery of engineered mutant strains.
Figure 8B:
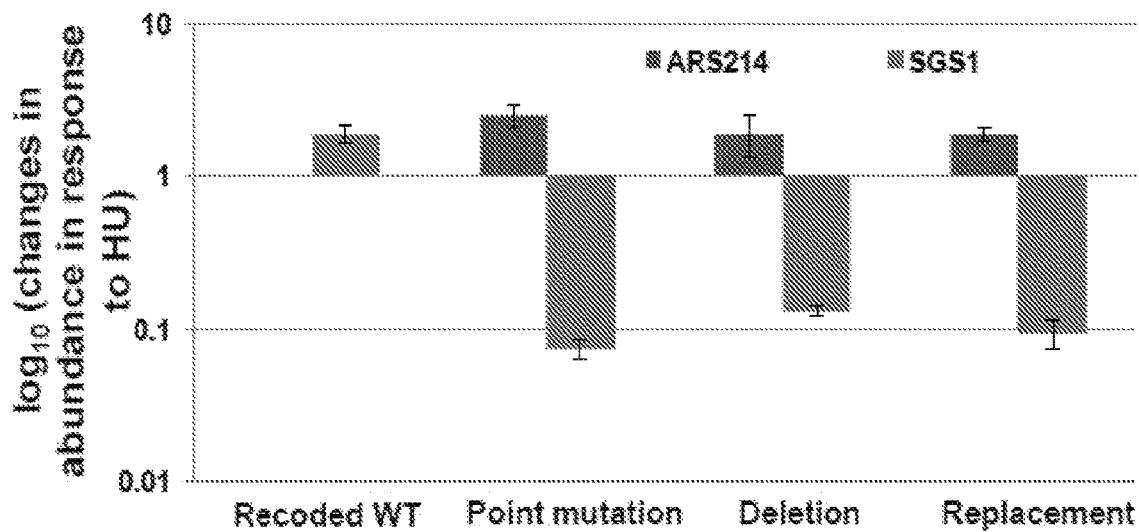
FIG. 8B depicts data demonstrating disablement of the SGS1 gene.
Figure 8C:
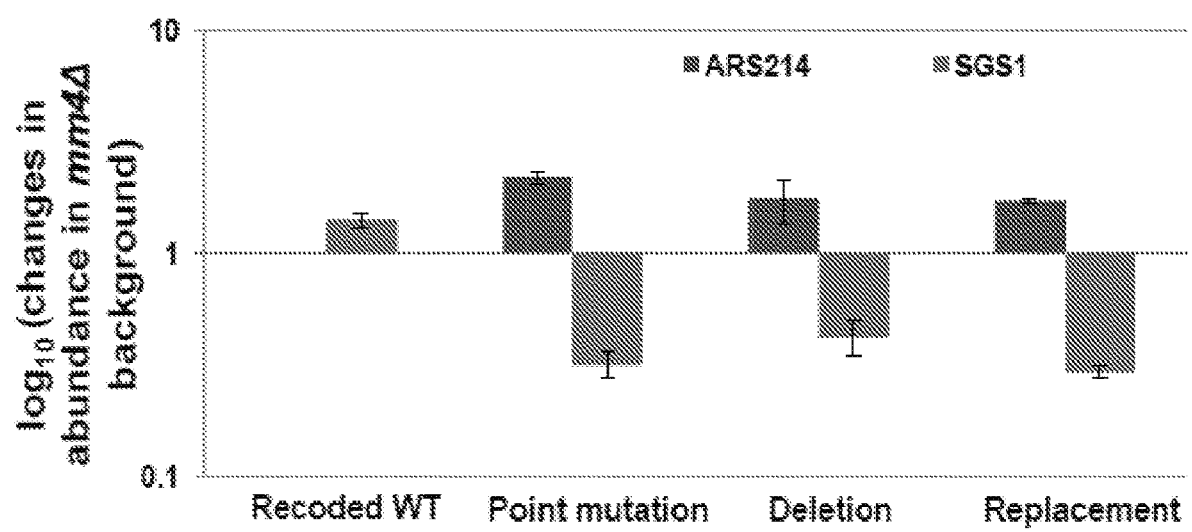
FIG. 8C depicts data evidencing changes in abundance in MMS4.

FIG. 8A is a bar graph of data demonstrating that the methods described herein allowed recovery of engineered mutant strains with 80-100% efficiency across different genomic sites and different types of mutations (point mutation, deletion, and replacement with GS linker). To demonstrate the feasibility of the method at library scale, an allelic series of mutants within SGS1 was created. SGS1 is a DNA helicase with critical roles during DNA repair and resistance to DNA damaging agents such as hydroxyurea (HU). The resulting library of transformants was next subject to HU and cells which received a gRNA+donor designed to disable the SGS1 gene saw a marked drop in their abundance (See FIG. 8B). Furthermore, the applicability of methods described herein in dissecting the genetic interactions between SGS1 with MMS4, encoding a structural endonuclease that is required for cell viability in the absence of SGS1 is demonstrated as indicated in FIG. 8C.

Example 4—Transformation of Yeast with Sgs1-Amino Acid Library

Figure 9:
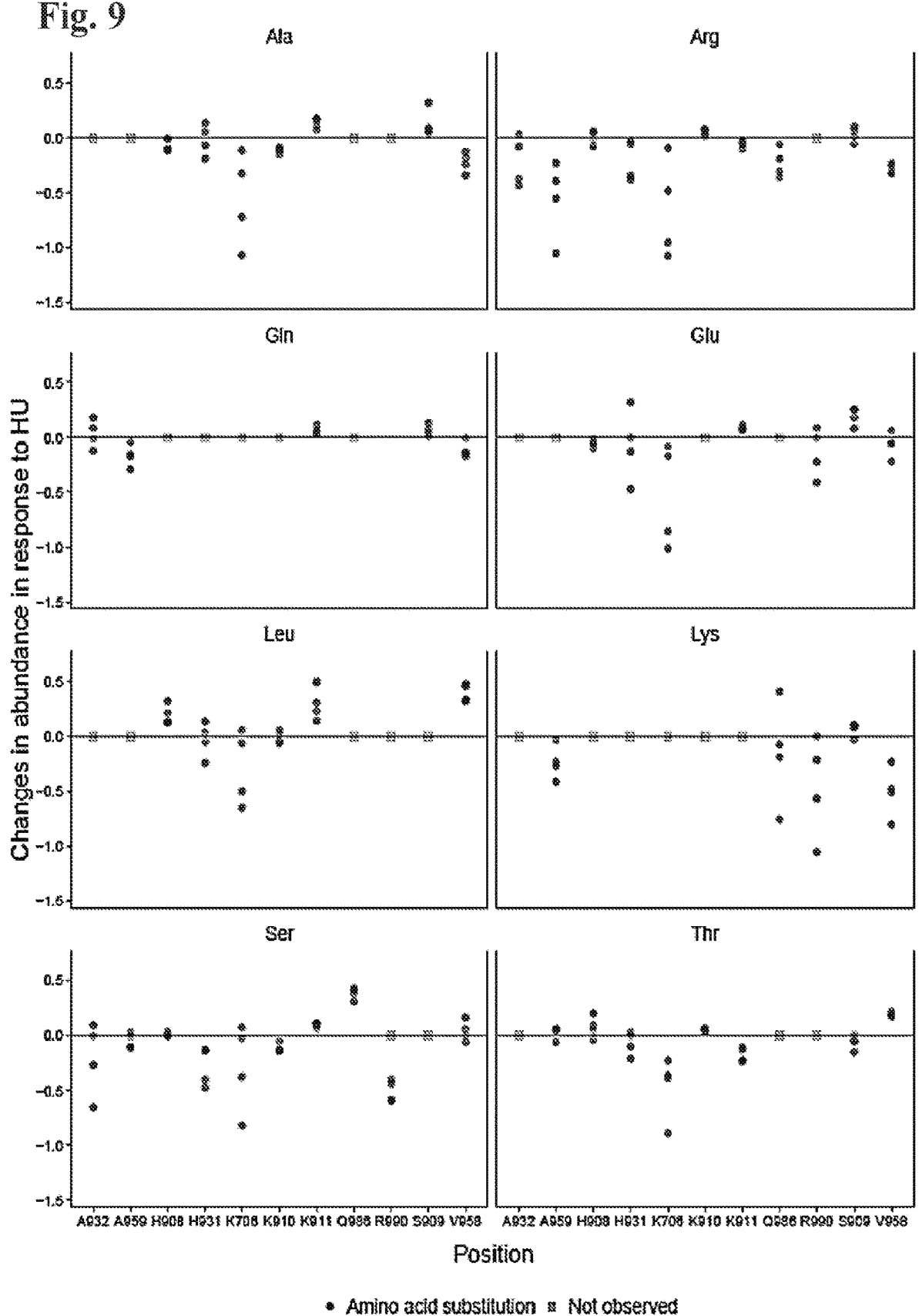
FIG. 9 depicts data evidencing changes in amino acid abundance in response to hydroxyurea.
Figure 9:
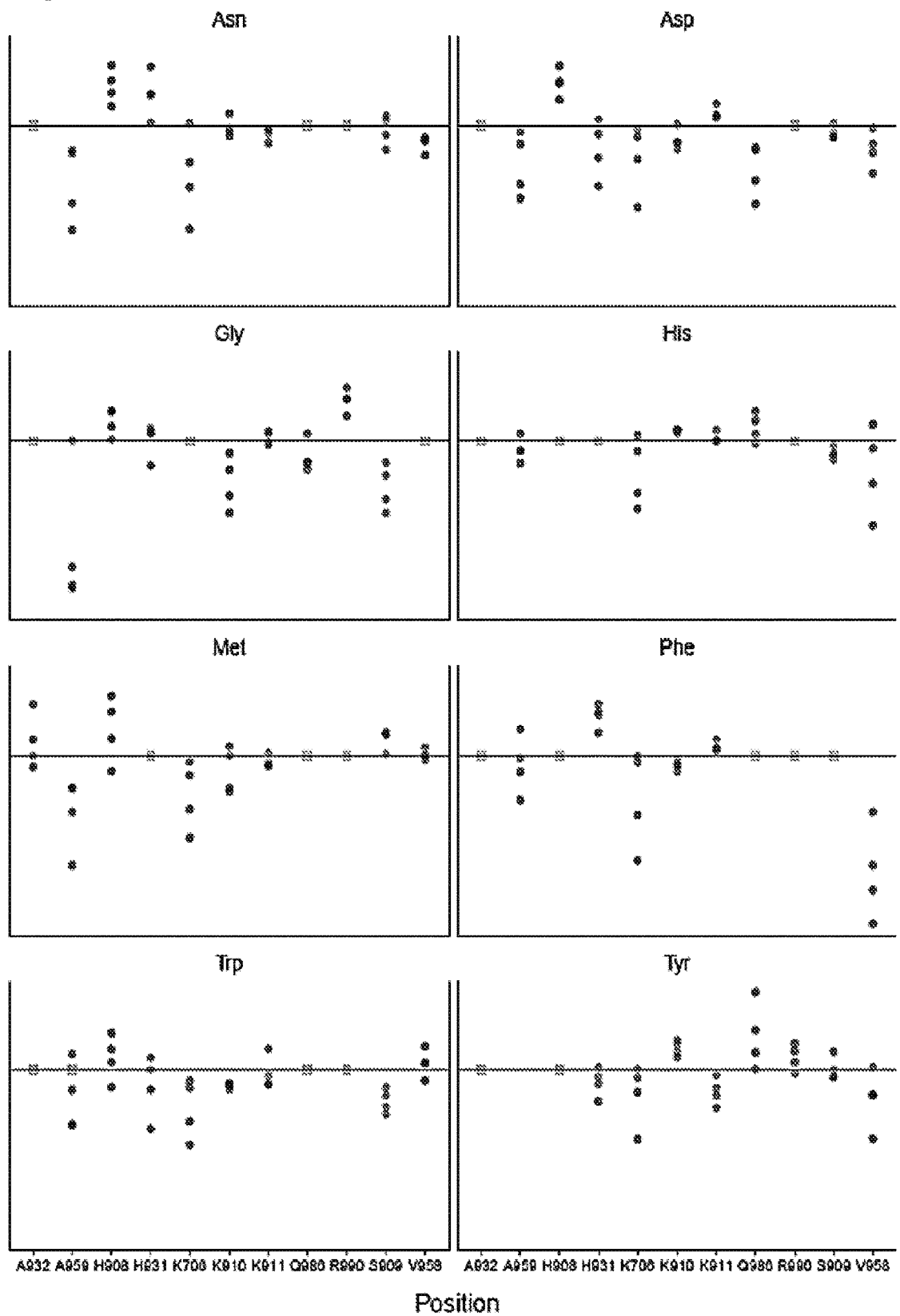
Figure 9:
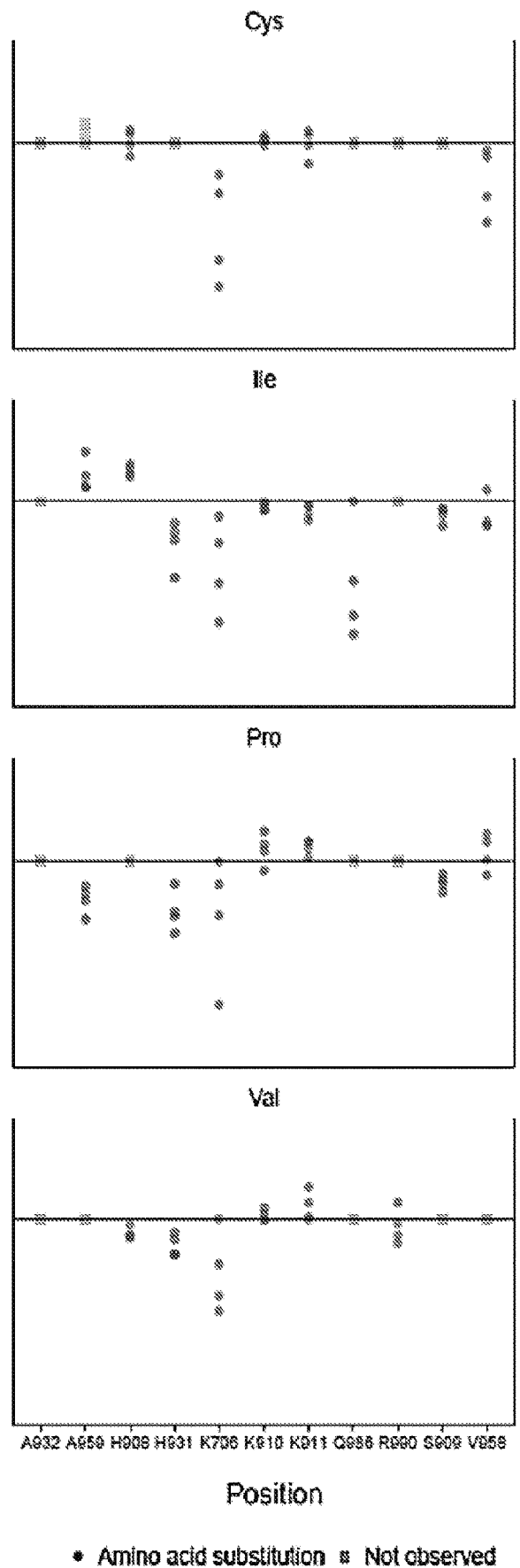

FIG. 9 depicts data for altered amino acids. The transformation of yeast with Sgs1-amino acid library designed to contain all possible amino acid changes for selected conserved residues and catalytic residue (K706) was carried out. Upon treatment to various concentration of HU, cells carrying guide+donors that altered catalytic residue K706 to other amino acids showed depletion. In addition, depletion signal was detected when certain conserved residues were mutated to certain amino acids.

REFERENCES

The disclosure of each reference cited is expressly incorporated herein.

5  Gietz, R. D. and R. H. Schiestl (2007). "High-efficiency yeast transformation using the LiAc/SS carrier DNA/PEG method." Nat Protoc 2(1): 31-34.

The invention claimed is:

1. A method of generating a library of carrier plasmids in which the carrier plasmids carry a mutation in a nucleic acid segment of a target cell, wherein carrier plasmids within the library carry different mutations in the nucleic acid segment, the method comprising:
   synthesizing on an array a library of oligonucleotides, each oligonucleotide comprising:
   (a) a segment encoding a guide nucleic acid which is complementary to a target site in a nucleic acid in the target cell, and
   (b) a donor DNA comprising the target site which is flanked by two sequences which are complementary to two regions of the nucleic acid of the target cell, wherein the two regions are on opposite sides of the target site, wherein the donor DNA consists of a single nucleotide mutation or more within the target site; and
   recombining the library of oligonucleotides with a backbone plasmid,
   wherein the oligonucleotides and the backbone plasmid recombine to form a circularized plasmid in which the segment encoding the guide nucleic acid is operably linked downstream from a promoter, wherein the donor DNA in the library of oligonucleotides comprises at least 24 distinct mutations each on a separate molecule of donor DNA.

2. The method of claim 1 wherein the circularized plasmid comprises a terminator downstream of the segment encoding the guide nucleic acid.

3. The method of claim 1 wherein the step of recombining is performed in vitro.

4. The method of claim 1 wherein the step of recombining is performed in vivo in cells.

5. The method of claim 1 wherein the backbone plasmid is linearized prior to the step of recombining.

6. The method of claim 1 wherein the circularized plasmid comprises a DNA barcode.

* * * * *